United States Patent [19]

Chow et al.

[11] Patent Number: 5,275,951
[45] Date of Patent: Jan. 4, 1994

[54] LIQUID LEVEL SENSING METHOD AND DEVICE

[75] Inventors: Herbert S. Chow, Palatine; John J. Kotlarik, McHenry; Mieczyslaw Wroblewski, Lake Forest; Thomas J. Wilson, Antioch, all of Ill.; Jimmy D. McCoy, Keller, Tex.

[73] Assignee: Abbott Laboratories, Abbott Park, Ill.

[21] Appl. No.: 939,570

[22] Filed: Sep. 3, 1992

Related U.S. Application Data

[62] Division of Ser. No. 714,810, Jun. 13, 1991, abandoned.

[51] Int. Cl.$^5$ ............... G01F 23/00; G01F 23/28
[52] U.S. Cl. ........................ 436/50; 422/67; 422/100; 422/106; 73/290 R; 73/304 C; 73/864.02; 73/864.24; 137/392; 436/149
[58] Field of Search ............... 422/67, 100, 106; 73/290; 137/392; 436/50

[56] References Cited

U.S. PATENT DOCUMENTS

| | | | |
|---|---|---|---|
| 3,582,285 | 6/1971 | Hamilton | 422/100 X |
| 4,318,886 | 3/1982 | Kawahara et al. | 422/82.05 |
| 4,326,851 | 4/1982 | Bello et al. | 422/63 |
| 4,431,307 | 2/1984 | Suovaniemi | 422/102 X |
| 4,599,315 | 7/1986 | Terasaki et al. | 422/102 X |
| 4,676,951 | 6/1987 | Armes et al. | 422/102 X |
| 4,727,033 | 2/1988 | Hijikata et al. | 422/65 X |
| 4,736,638 | 4/1988 | Okawa et al. | 73/304 C X |
| 4,738,534 | 4/1988 | Houseman et al. | 436/527 X |
| 4,738,824 | 4/1988 | Takeuchi | 422/65 X |
| 4,818,492 | 4/1989 | Shimizu | 422/63 X |
| 4,835,707 | 5/1989 | Amano et al. | 422/67 X |
| 4,897,244 | 1/1990 | Wallace et al. | 422/100 |
| 4,912,976 | 4/1990 | Labriola, II | 73/290 R |
| 4,925,629 | 5/1990 | Schramm | 422/65 X |
| 4,977,786 | 12/1990 | Davis | 73/864.24 |
| 5,027,075 | 6/1991 | Harding, Jr. | 324/662 |
| 5,041,266 | 8/1991 | Fox | 422/57 X |

FOREIGN PATENT DOCUMENTS 0212663 3/1987 European Pat. Off. ............ 422/100

OTHER PUBLICATIONS

Fiore et al. "The Abbott IMx TM Automated Benchtop Immunochemistry Analyzer System," *Clin. Chem.*, 1988, 34, 1726-1732.

*Primary Examiner*—James C. Housel
*Assistant Examiner*—Robert Carpenter
*Attorney, Agent, or Firm*—Richard D. Schmidt

[57] ABSTRACT

An apparatus is provided which includes a reaction cartridge having a plurality of reaction wells having different reagents disposed thereon, at least one well adapted to receive a sample, a well containing particles adapted to bind to the sample and which have the capability of being separated from cells which are not bound to the separation particles and at least one fluorophore adapted to bind to a specific type of cell in the sample, and a wash area adapted for washing a probe. An image forming device is provided to detect images which indicate whether specific reactions have occurred in each of the reaction wells. The apparatus also includes a mechanism for dispensing and aspirating liquids including a mechanism for detecting liquid levels. The device further includes logic for analyzing the information received from the image detection apparatus and processing the information to generate a visual indication of the results of the assays being performed. A microprocessor is provided to assist in the operation of the device as well as in the image processing.

15 Claims, 12 Drawing Sheets

LIQUID LEVEL SENSING METHOD AND DEVICE

This is a division of U.S. Ser. No. 07/714,810 filed Jun. 13, 1991, now abandoned.

BACKGROUND OF THE INVENTION

The present invention relates generally to an automated apparatus and method for performing assay testing on specimens, such as biological specimens. More specifically, the invention is directed to an automated apparatus and method for assay procedures to detect the compatibility of tissue or blood from a donor to a recipient.

Modern test procedures for determining or measuring the optical or electrochemical development of unknown specimens are used extensively in a number of medical testing procedures. In such tests, sample specimens are reacted with reagents and other substances. Such known procedures involve a variety of different assay steps but typically rely on detection and measurement of optical changes in a sample or label during the assay procedure. For example, a number of well known procedures use single or multi-wavelength fluorescence. These and other immunoassay techniques are known as Fluorescence Polarization Immunoassay (FPIA), solid phase agglutination, stained cellular morphology, Enzyme Immunoassay (EIA), chemolumination, spectrophotometric assays.

Other currently used assay techniques are effected by exposing the resulting sample to either transillumination or reflectant illumination. These assay procedures involve detecting the intensity of colorization, detecting ratio of multiple wavelengths of colorization, detecting the polarization in the sample, determining the size and quantity of specific cells at certain wavelengths, the general cell morphology or other optical characteristics of the results. The data from these procedures is then processed in a known manner to obtain the concentration or ratio of the component (or components) of interest. These techniques, however, have not been completely accepted and usually manual analysis is also performed as a check or verification.

One assay procedure of particular interest is a procedure known as Human Leukocyte Antigen (HLA) typing. This procedure is employed in matching tissue, body organs or blood from a donor to a recipient. In this HLA procedure, lymphocytes in samples containing human cells are first reacted with different antisera. The cell-serum mixture is then incubated with a complement. One or more stains are added to the mixture, with one of the stains staining dead cells. The reactions are then evaluated by calculating the ratio of dead cells (lyced cells) to live cells. The calculations are performed by using a microscope and estimating the ratio. This ratio is converted into a "score" ranging from 1-8 by using a well-known value scale.

In this HLA procedure, as well as other assay procedures, paramagnetic particles are coated with an antibody. The paramagnetic particles are then mixed with a sample to be analyzed. The antibody on the paramagnetic particles binds to specific cells in the sample. These specific cellular components may then be separated from the other cells in the population which is being tested using magnetic separation techniques. Alternatively the cells may be separated by using a nylon wool column. After the cells have been reacted with the antibody, the sample mixture is subjected to a series of operations such as particle exposure, reagent exposure, incubation, and washing. The cells in the sample may also be stained with one or more chemical markers as discussed above with respect to HLA assays. The sample is then analyzed. Typically, the sample will be analyzed manually by the technician. This manual analysis usually involves a visual analysis to determine the approximate percentage of the cells which have reacted with the antibody.

A significant shortcoming of these and other available assay techniques is that most of the steps in the procedure must be performed manually. For example, most of these procedures require manual preparation of the sample. Further, steps such as dispensing, mixing, washing, incubation, data collection, scoring and recording are also performed manually. Thus, most available assay techniques require a significant amount of human operator time.

As will be apparent to those skilled in the art, manual performance of these steps is also undesirable since it results in numerous opportunities for errors to occur. This is especially true for highly repetitive functions. The probability of errors is further amplified by the fact that many of these procedures require pipetting of very small volumes, i.e. usually of sub-microliter volumes. Further, scoring of thousands of reactions using a microscope and pencil also increase the probability of errors in the analysis.

A further drawback is the subjectivity which is permitted to the individual performing the test. This subjectivity may lead to inconsistent results, not only from assay to assay, but inconsistent analysis during the numerous repetitions in the same assay.

Although some available HLA assay devices automate individual steps, most of the steps in these devices are still performed manually. For example, U.S. Pat. No. 4,318,886 (Kawahara et al.) discloses an apparatus for HLA typing which uses a phase-contrast microscope and an optical image to generate a signal which is detected by an electrical signal pickup unit. The image is then binarized and compared with predetermined template patterns corresponding to reacted or nonreacted lymphocyte. Although the scoring of the results is automated, the preparation, incubation and washing of the sample must still be performed manually by the operator.

Further, this apparatus uses dedicated electronic hardware to score the HLA typing test. As discussed in more detail below, anomalies such as dirt or dust in the sample, scratches in the sample container, or unusually large cells would result in unreliable or erroneous results. In fact, without redesign for such possible variations, many human readable samples are unreadable by this apparatus. Variations in the procedures used by the operator preparing the samples may also lead to unreliable results without major redesign of the system. In summary, any expansion of the apparatus to score assays other than those it was specifically designed for is difficult and costly, requiring major redesign of the hardware for each assay.

Another major disadvantage of available automated systems, such as the one disclosed in U.S. Pat. No. 4,318,886, in that they are designed for a specific assay procedure (such as HLA typing). It is not possible to perform assays for which the instrument was not originally designed without major redesign of the hardware and or software. Such major redesign is impracticable and thus the use of available instruments is limited to a single type of assay.

Precise dispensing of the sample in reaction wells is also critical for accurate assay results. In HLA typing the dispensing is usually performed manually. A typical manual dispensing operation may include dispensing sample volume of from 0.5 μl to 1.0 μl into a volume of from 0.5 μl to 2.0 μl of a reagent which is covered by from 2.5 μl to μl of mineral oil. (The oil is used to prevent evaporation of the reagents.) It will be appreciated that performing this dispensing step involves a significant amount of operator time, which increases as the number of different reagents increases. Further, the operator will usually insert the tip of the pipette below the bottom surface of the oil and into the reagent itself. In order to prevent carryover from one reaction site to the next, the operator will typically manually wipe the tip of the probe thus consuming more operator time and increasing the chances for erroneous results.

If automated assay apparatus and methods are to be used in HLA assay procedures, they must be capable of very precise monitoring of liquid levels and precise control of liquid dispensing mechanisms (such as a pipette). Precise dispensing mechanisms are particularly important in HLA typing since, as discussed above, very small volumes of liquids (sub-microliters) have to be dispensed usually into a container which contains another liquid. Although some automated liquid dispensing systems are presently available, they are not completely suited for dispensing liquids in assays such as HLA typing. Available automated liquid dispensing systems usually work by detecting the liquid level in a container and then determining the position of the dispensing probe relative to the liquid surface. This information is then used to determine when the probe tip is within the liquid in the sample container. After the liquid surface has been detected and it has been determined that the probe is in the fluid, fluid may be dispensed into or aspirated from the container. The precision of the liquid dispensing system will thus depend in part on the precision of the liquid level detection.

The limited potential for available liquid level detection and fluid dispensing systems in HLA assay typing is due to the fact that they typically use a capacitance method to detect the liquid surface as a pipetting probe moves towards the liquid in a sample container. Dispensing liquids in volumes smaller than one microliter is complicated in such capacitive or conductance systems since the oil which covers the reagent has a low dielectric constant. The dielectric constant of oil is only two times greater than the dielectric constant of air rendering most capacitive detection methods unreliable for detection of the oil surface. Further, because of the high resistivity of the oil, available conductance methods cannot be used accurately.

Available capacitive type dispensing systems also do not have any means for determining when a droplet of the sample is formed on the dispensing probe or when a droplet of the sample has been separated or released from the probe tip. The ability to detect the occurrence of one or both of these events is important information which could be used to improve the accuracy and reliability of the dispensing system.

Therefore, it would be desirable to have a liquid level detection and liquid dispensing arrangement capable of detecting very small amounts of liquid (down to fractions of a microliter) and with the capability of detecting the level of a liquid having a low dielectric constant.

Another area of assay testing where significant improvements are necessary is in the area of image processing used for counting reactions. Although photomultiplier tubes have been previously used in some HLA readers, they are not without disadvantages and have not been readily accepted in the market. These readers use the photomultiplier tube as a fluorescent densitometer to measure the overall light output from the reaction site for each wavelength. This is acceptable for ideal samples but produces critical errors if any contaminants, such as dirt, dust, or other interfering substances or other anomalies, such as scratches, are in the reaction site. The errors arise because this approach cannot determine the features in an object, such as shape or size of particulates in the reaction site. Therefore, there is a need for an instrument with improved discriminations of features within the field of view of the imaging device. Although higher magnification and selective mask techniques may be developed for the photomultiplier tube to yield the desired selectivity, the cost, reliability and throughput of such a device would make it impractical. In addition, such devices do not produce an image to which a human technician is accustomed and therefore it would be difficult for a technician to score the results on that image to confirm the instrument generated results.

Therefore, in view of the above it is a primary object of the present invention to provide an apparatus and method for automatic processing of a qualitative, quantitative or morphological analysis of test specimens including serum, plasma or cellular components as well as other non-biological specimens.

It is another object of the present invention to provide an automated instrument for performing HLA typing, including automated cell preparation, automated sample processing, and automated reading of the results.

It is a further object of the present invention to provide an apparatus and method for performing an assay on a disposable or reusable cartridge on which the specimen to be analyzed may be placed and which will be analyzed by an automated instrument.

It is another object of the present invention to provide an analytical instrument with a liquid dispensing and liquid level detection system which can control liquid dispensing of very small volumes, accurately determine liquid levels even in liquids with a relatively low dielectric constant, and determine droplet formation and separation.

It is another object of the present invention to provide a detection system which can detect the interface between liquids with different dielectric constants.

It is another object of the present invention to provide an analyzing instrument with powerful, cost-effective and efficient image processing for automated sizing and counting of data.

It is yet another object of the present invention to provide an apparatus which is field upgradeable to perform different types of assays.

SUMMARY OF THE INVENTION

To achieve these and other objects, the present invention comprises an apparatus which automates the steps required in an assay procedure including cell preparation, sample processing, dispensing and scoring of the assay results.

The apparatus of the present invention includes an image forming arrangement i provided to detect images which indicate whether specific reactions have occurred in each of a plurality of reaction wells on a reaction cartridge. The apparatus also includes a mechanism for dispensing and aspirating liquids including a mechanism for detecting liquid levels. The device further includes logic for analyzing the information received from the image forming arrangement and for processing the information to generate a visual indication of the assays being performed and their results. A microprocessor is provided to assist in the operation of the device as well as in the image processing. The apparatus performs the assays on a reaction cartridge having a plurality of reaction wells having different reagents disposed thereon. At least one well is provided in the reaction cartridge to receive a sample. The cartridge includes a well for containing particles adapted to bind to the sample and which have the capability of being separated from cells (such as paramagnetic particles) which do not bind to the separation particles. A well with at least one fluorophore adapted to bind to a specific type of cell in the sample is also provided. The cartridge includes a wash area adapted for washing a probe.

In another aspect of the invention, a particularly novel configuration for a cartridge which may be used in the apparatus and methods of the present invention is provided. The cartridge includes a plurality of reaction wells having different reagents disposed therein. The cartridge also includes unit volumes of separation particles, a well adapted to receive a unit volume of the sample to be analyzed, and a well for storing a unit volume of dye (such as a fluorescent dye) which may be used in the analysis of the sample. The cartridge also preferably includes a well which may be used as an area for washing a dispensing probe and for holding waste.

In another aspect of the present invention, a particularly unique arrangement is provided for detecting multiple liquid levels and dispensing fluids. The liquid level and dispensing mechanism includes a probe through which a fluid is dispensed. The system includes the ability to detect when a droplet has been formed by the probe and when the droplet has been separated from the probe. An oscillator provides a radio-frequency signal to the tip of the probe. A conductive element connected to amplifying and analyzing circuitry is disposed below the dispensing probe and the reaction well. The conductive element receives the radio-frequency signal from the probe and processes the signal to determine when the probe has reached the surface of a liquid in the well, when a droplet has been formed and detached from the probe, and when the probe is inserted into the liquid.

Additional objects, advantages and novel features of the invention will be set forth in part in the description which follows, and in part will become apparent to those skilled in the art upon examination of the following or may be learned by practice of the invention. The objects and advantages of the invention may be obtained by means of the combinations particularly pointed out in the appended claims, including all equivalents.

DETAILED DESCRIPTION OF THE PRESENTLY PREFERRED EMBODIMENTS

System Architecture

Figure 1:
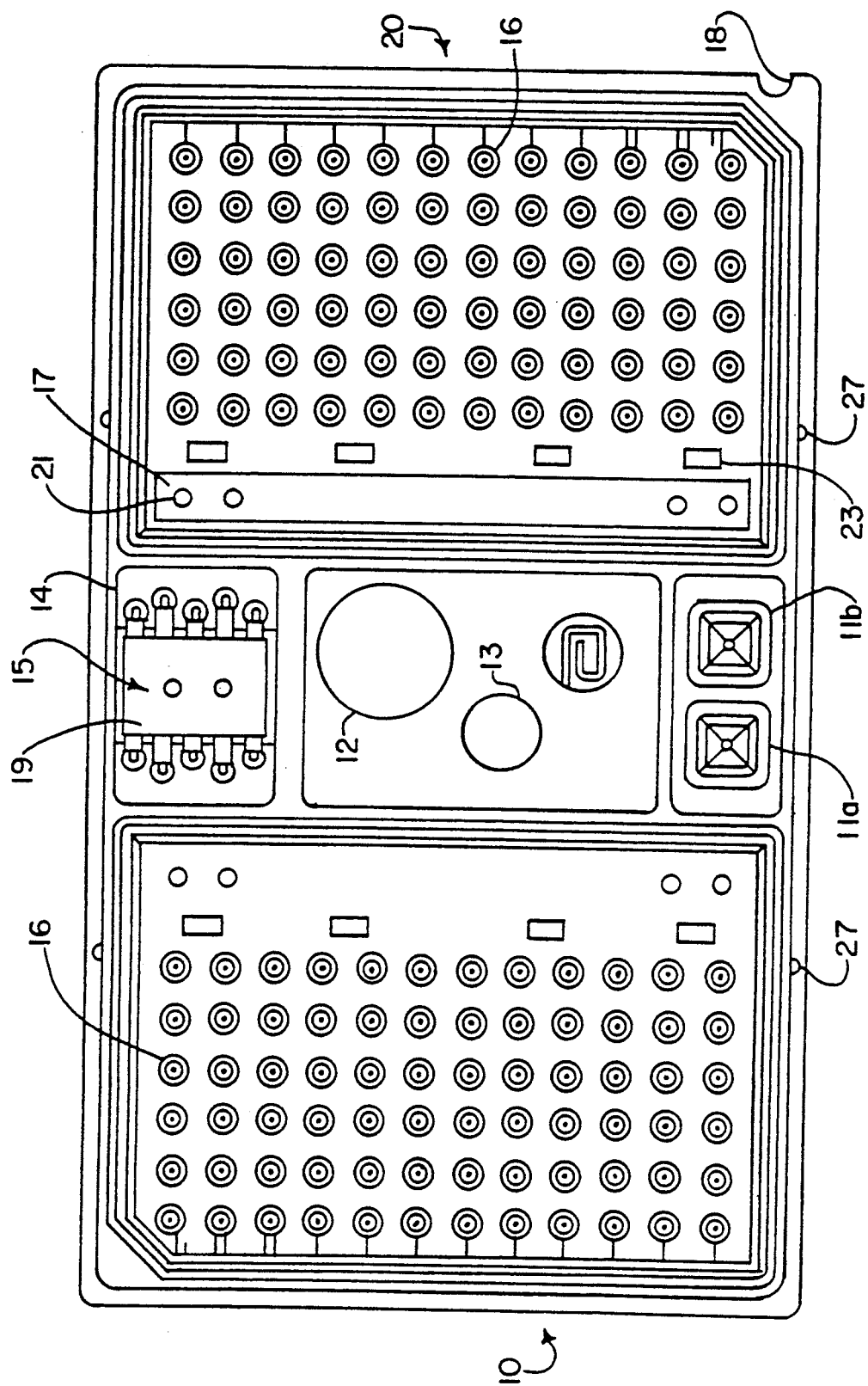
FIG. 1 is a preferred embodiment of a cartridge of the present invention for holding reagents and samples to be analyzed.

Referring now to the drawings, FIG. 1 illustrates a preferred embodiment of a test cartridge 10 which is used in the analysis of the specimens to be tested. In the embodiment illustrated in FIG. 1, the cartridge 10 is particularly suited for HLA tissue typing. Although this and other embodiments which will be described are directed to HLA analysis, it will be readily apparent to those skilled in the art that the disclosed apparatus and methods may also be used with other assay procedures.

The tray or cartridge 10 includes two sample wells 11a and 11b. The second well may be used as a redundant sample well which holds a sample for a second attempt at using the cartridge if the first sample does not provide satisfactory results. The sample cartridge 10 also includes a reagent well 12 which is used for storing paramagnetic particles and a fluorescent dye or fluorophore. The fluorescent dye may be, for example, of blue excitation and green emission wavelengths. A well 13 contains a complement reagent and a second fluorophore. The second fluorophore preferably excites at green and emits at red wavelengths. The cartridge 10 also includes a probe wash area 15 with a plurality of separate wash basins 14 (ten shown). The wash basins 14 drain off into the center of the probe wash area 15. Preferably a blotter 19 is disposed in the center of the probe wash area. The blotter 19 absorbs excess fluid to prevent splashing or spilling during transport of the cartridge 10. Since the blotter 19 absorbs the waste fluid, it also facilitates the disposal of these wastes since they are now in solid form and may be disposed with the cartridge 10 itself. Preferably the blotter material is chosen to define a biaxial transorb reservoir in the probe wash area 15. A suitable blotter material is a bonded cellulose acetate, such as is available from American Filtrona Co. (Richmond, Va.).

As illustrated, the cartridge 10 includes a plurality of reaction wells 16. In the embodiment illustrated in FIG. 1, the cartridge 10 includes 72 reaction wells on each side of the center area of the cartridge 10. Thus, in the preferred embodiment a total of 144 or more reaction wells 16 are provided. The reaction cartridge 10 may also include blotter material 17 to absorb reaction and wash fluids. The blotter 17 is held in the cartridge 10 by means of pins 21 and ribs 23.

Thus, the cartridge 10 advantageously provides an arrangement where unit doses of the required reagents, dyes and separation particles and a well for a unit sample are provided. Additionally, this configuration permits the automation of the assay steps.

Figure 2:
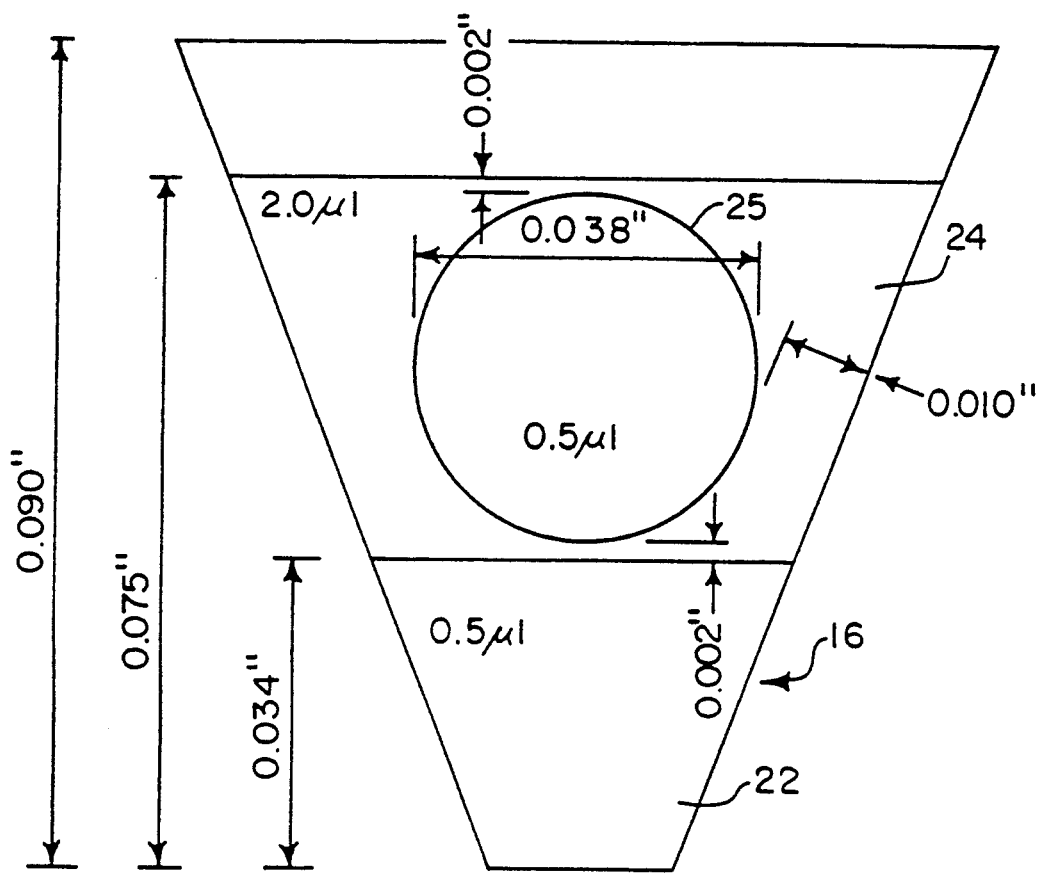
FIG. 2 is a preferred embodiment of one of the reaction wells in the cartridge illustrated in FIG. 1 depicting reagents and a droplet in the well.

Referring now to FIG. 2, a preferred configuration for the reaction wells 16 of the cartridge 10 is illustrated. Each of the reaction wells preferably has a 0.020 inch diameter bottom and a 0.090 inch top diameter and a height of 0.090 inches. The reaction wells may be formed on a cartridge made of mineral oil free, high-grade polystyrene by known techniques, such as injection molding. The inner surface of the reaction wells 16 is preferably plasma treated by known gas plasma (or gas ionization) treatment techniques, such as by the techniques disclosed in the article entitled "Treating Plastic Surfaces With Cold Gas Plasmas", P. Rose et al., Plastics Engr., Oct. 1, 1980, which is incorporated herein by reference. In the embodiment which is illustrated in FIG. 2, each reaction well 16 has 0.5 microliters of antisera 22 covered with 2.0 microliters of an oil (such as mineral oil) to prevent evaporation. As will be recognized by those skilled in the art, the amount of oil may be varied in the well. For example, the well may contain 2.0 or 2.5 microliters of oil. FIG. 2 also depicts a droplet 25 containing 0.5 microliters of sample which has been dispensed in the layer of oil 24.

Figure 3:
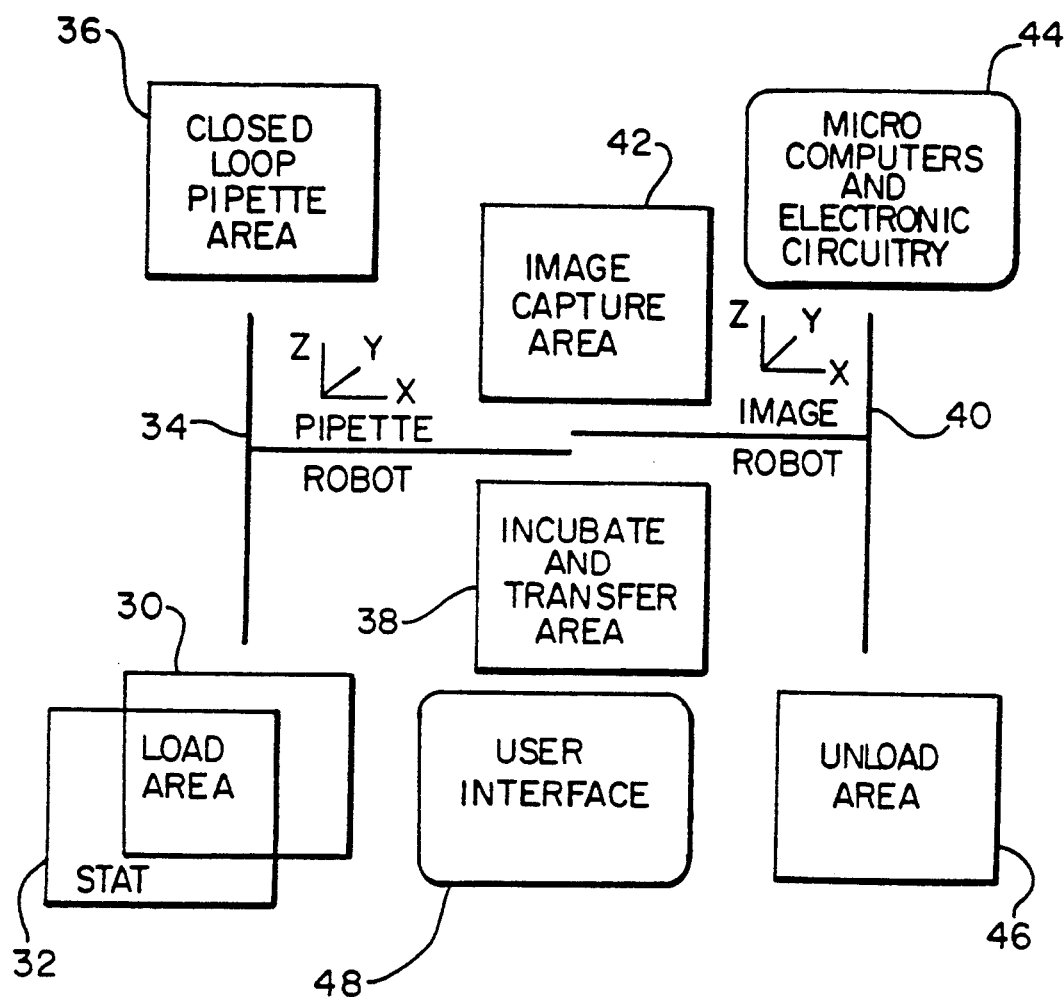
FIG. 3 is a block diagram of a preferred embodiment of the major components of the analyzing arrangement of the present invention.
Figure 4:
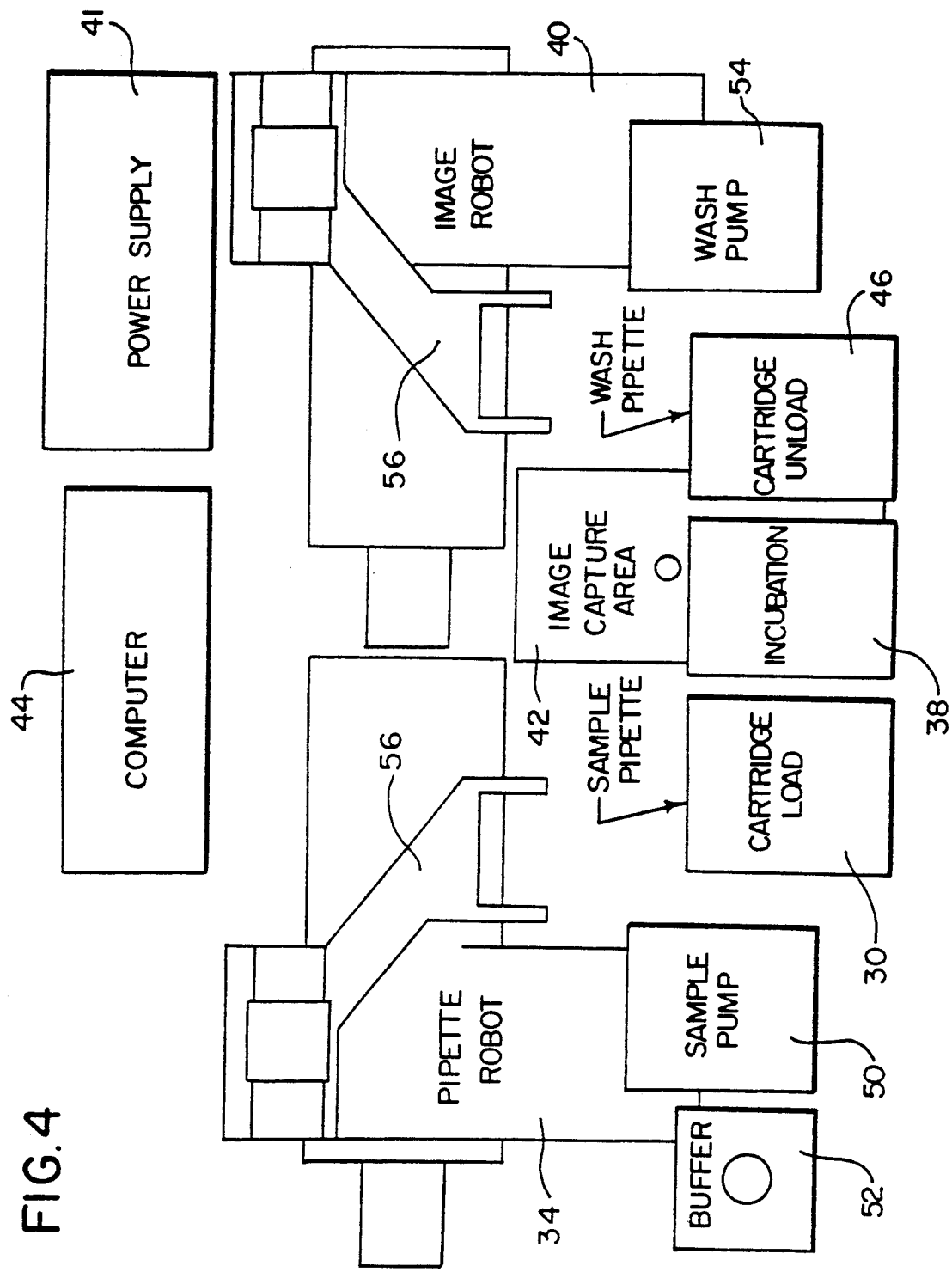
FIG. 4 is a schematic block diagram of a top view of the preferred embodiment of the apparatus and method illustrated in FIG. 3.

Referring now to FIGS. 3 and 4, the major components of a preferred embodiment of the apparatus of the present invention is illustrated in block diagram form. The apparatus includes a load area 30 and a stat load area 32. The stat load area 32 may be used to hold cartridges 10 with a higher priority than those in load area 30. Thus the cartridges 10 loaded into stat load area 32 will be processed first. The cartridge 10 illustrated in FIG. 1 is inserted manually into either load area 30 or stat load area 32. Each of the pipette robot 34 and the image robot 40 (discussed in more detail below) includes a gripper which grasps the cartridge 10. One of the pipette robot 34 and the image robot 40 moves the cartridge 10 from the load or stat area and transports the cartridge 10 to an image capture area 42. Preferably the cartridge 10 includes a key 18 which is used to align or orient the cartridge 10 in the gripper of the robot. The image capture area 42 may include means for taking an image of tray labeling information, such as barcode or optical character recognition (OCR) type information. This information may be used to determine the desired assay or assays for the particular cartridge which is to be analyzed, and to record any sample or patient identification information. The information may then be stored in a database for subsequent management tasks.

The apparatus includes microcomputer and electronic circuitry 44 which will schedule the operations required to complete the desired assays after the assay requirements have been identified in a manner known in the art.

Preferably, the apparatus also includes a user interface 48 which may be used by the operator to manually enter information into the microcomputer memory or to download such information via a serial communications interface or read such information from a removable magnetic device.

As illustrated in FIG. 4, the apparatus also includes a container for the buffer 52, a power supply 41, a sample pump 50 and may optionally include a wash pump 54.

Figure 5:
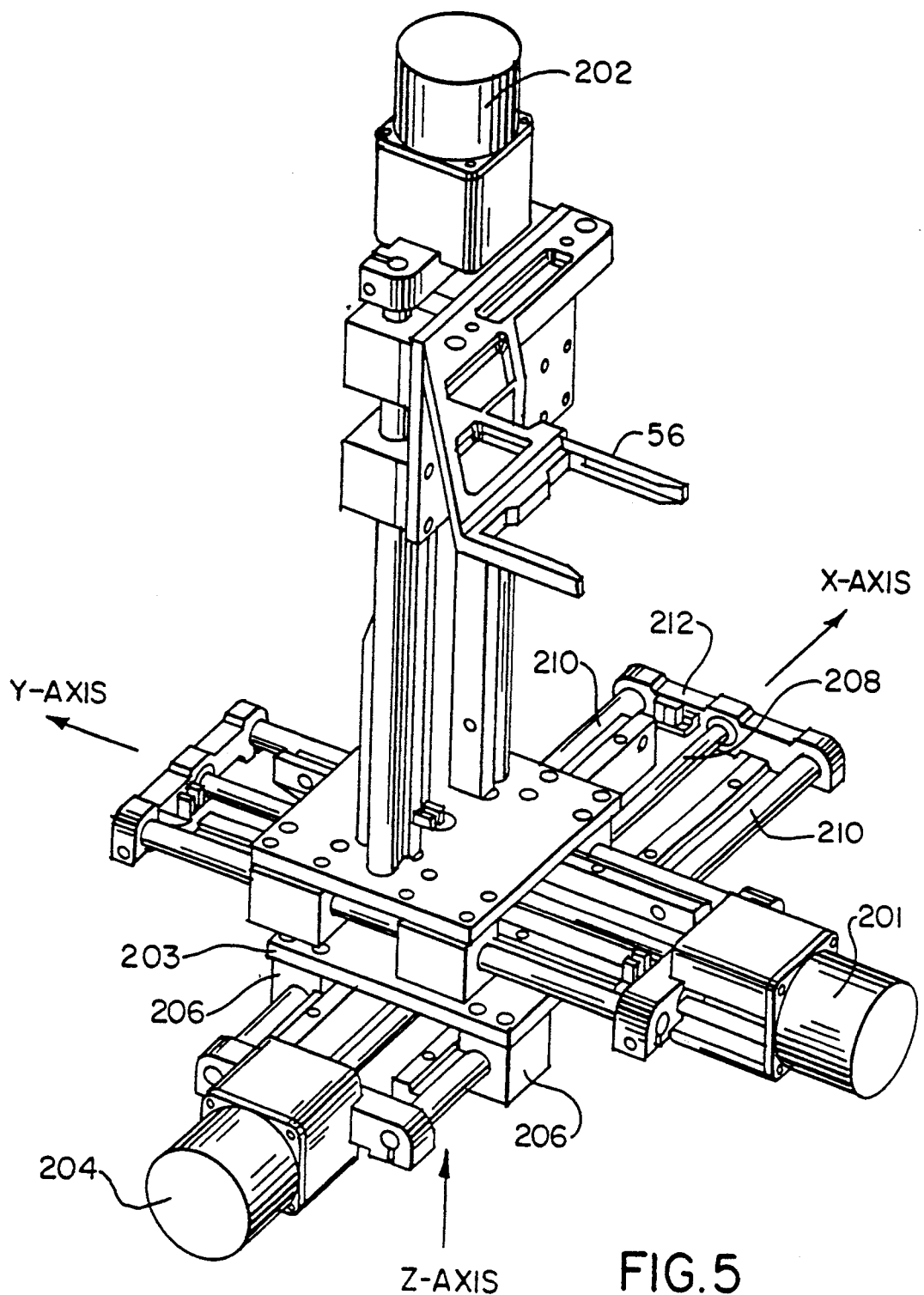
FIG. 5 is a preferred embodiment of a three axis robot including a gripper which may be used for the pipette and image robots illustrated in FIGS. 3 and 4.

The pipette robot 34 and the image robot 40 may be any suitable three axis robot. FIG. 5 illustrates one presently used embodiment. The three axis robot comprises three stepper motors 201, 202, and 204 which cooperate with respective translating screws to move a gripper arm 56 to a desired position. A brief description of the movement assembly in the X-axis is given here. It will be recognized by those skilled in the art, that the movement in the Y-axis and Z-axis will be performed in a similar fashion.

The X-axis movement assembly comprises the stepper motor 204 which is connected to a translating screw 208 to provide translational motion of a platform 203 which supports the remaining robot assembly. Guide rails 210 and cooperating linear bearings 206 are provided to stabilize the translational movement in the X-direction. Switches 212 are provided to determine the position and control translational movement in the X-direction.

In a preferred embodiment, the normal working stroke of the X-axis and the Z-axis will be 6.75 inches while the working stroke in the Y-axis will be 5.75 inches. Each axis would preferably be capable of positioning with a minimum accuracy of +/− from about 0.001 to about 0.003 inches over the entire length of travel. The assembled three axis robot will preferably be capable of positioning with a minimum accuracy of +/− from about 0.001 to about 0.005 inches over the entire travel of each axis. A minimum resolution of 0.001 inches per 1.8 degree step input (200 steps/rev.) is preferable for each axis. Preferably, each axis shall be driven by a 200 step/rev., 4 phase, 8 wire stepper motor. Each axis will preferably be capable of translating at a maximum velocity of 2.5 inches/sec. and be capable of translational accelerations for each axis of 25.0 inches/sec./sec. and a maximum translational deceleration, for each axis, of 50.0 inches/ sec./sec. Preferably, each stepper motor is connected to its corresponding translating screw through a zero-backlash coupling of the helical spring type or by direct connection. The X-axis would preferably have a position sensor at each end of travel, and the Y-axis and the Z-axis shall preferably have a position sensor at the motor end of travel.

Suitable three axis robots may also be available from commercial sources, for example one available as Model No. 105073P-20E from DAEDAC (Harrison City, Pa.).

Figure 6:
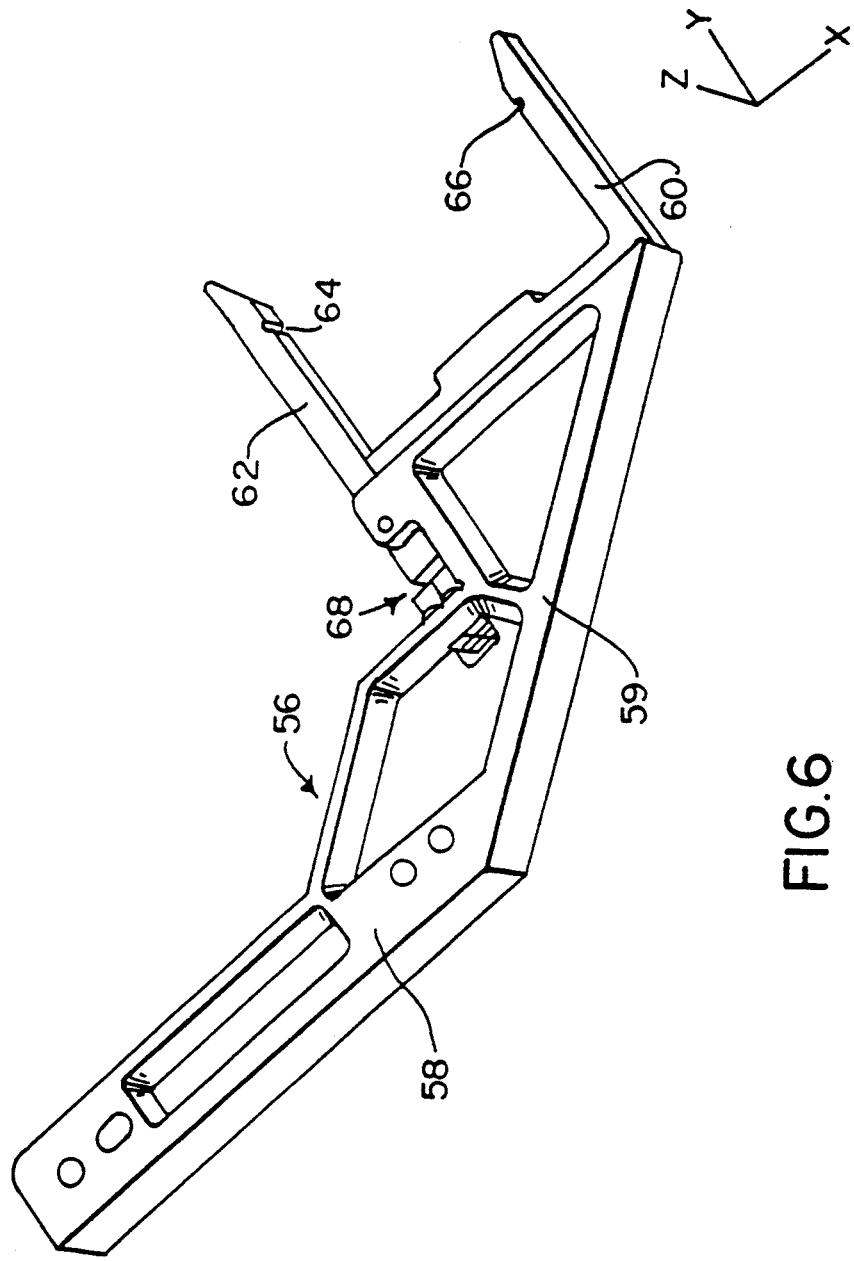
FIG. 6 is a preferred embodiment of the gripper which may be used in the three axis robot illustrated in FIG. 5.

As illustrated, three axis robots 34, 40 include a gripper arm 56. Referring to FIG. 6, the gripper arm 56 includes a base member 58 which is attached to the respective robot. The base member 58 is in turn attached to an angled member 59 which is in turn attached to a jaw assembly.

The gripper jaw assembly includes a fixed jaw 60 and a springloaded jaw 62. The gripper arm 56 is configured such that the jaws 60, 62 are disposed perpendicular to the axis of the base arm 58. Each of the gripping ends of jaws 60 and 62 is angled to facilitate the gripping of a cartridge 10.

Notches 64 and 66 are provided on gripper jaws 60 and 62, respectively. The notches 64 and 66 advantageously engage ribs 27 on the cartridge 10 to grip and align the cartridge 10.

During a gripping operation, the cartridge is centered between the gripper jaws 60 and 62. As the arm 56 is moved along the Y-axis toward the cartridge 10, the ribs 27 engage the inner surface of each of the gripper jaws 60 and 62, thereby slightly opening the springloaded gripper jaw 62. The gripper arm 56 is advanced in the Y-direction toward the cartridge 10 until the ribs 27 engage the notches 64, 66. When the ribs 27 have moved into the notches 64, 66, the springloaded gripper jaw 62 moves back to its unbiased position.

Advantageously, sensors 68 are provided to detect the alignment of springloaded gripper jaw 62. The detectors 68 will determine if the gripper jaw 62 is in the unbiased position when the cartridge 10 is inserted. This provides an arrangement to detect whether or not the cartridge 10 is properly positioned in the gripper arm before further processing. Suitable detectors are slotted optical switches sold under Model No. OPB990P51 such as those available from OPTEK (Carlson, Tex.).

In order to release the cartridge 10 from the gripping jaw assembly, the cartridge 10 includes a lip portion which extends downwardly from the gripper jaw assembly. The lip portion (not shown) may be, for example, a lip extending downwardly from one side edge of the cartridge 10 such as the side indicated by arrow 20. This lip portion is adapted to engage a fixed ledge (not shown) as the gripper arm 56 is moved away from the cartridge 10 along the Y-axis, the ledge and lip portion cooperating to release the cartridge 10 from the gripper jaw assembly.

The carrier 10 is then transported to a closed loop pipette area 36 where aspirating, mixing, dispensing, washing and/or particle separation operations are performed based on prestored information concerning the assay (discussed in more detail below). The pipette area preferably includes a magnet which is positioned near (preferably below) the reaction wells 16 during particle separation and washing procedures.

One of the image robot 40 and the pipette robot 34 then places the cartridge into an incubation transfer area 38. The cartridge 10 is held in the incubation area 38 for a predetermined incubation time period sufficient for the required reactions to occur. The incubation area 38 is preferably accessible from both the pipette robot 34 side of the device as well as from the side of an image robot 40. After the robot 34, 40 has moved a cartridge 10 into the incubation area 38 it is then free to begin processing another cartridge. Preferably, the robot 34, 40 has random access capabilities to allow it to return a cartridge 10 from the incubation area 38 to the pipette area 36 as many times as needed, determined by the prestored requirements of each assay.

Once all pipetting and incubation area processing has been completed for a specific cartridge 10, the image robot 40 then grabs the cartridge from the incubation/transfer area 38. The image robot 40 then transports the cartridge 10 to an image capture area 42 where image information is determined and converted into electrical information for further signal processing by the microcomputer and electronic circuitry 44 (described in more detailed below). Once all required images have been captured for a specific cartridge 10, the image robot 40 transports the cartridge 10 to an unload area 46.

The pipette robot 34 and the image robot 40 preferably operate independently of each other thereby allowing for parallel processing of the cartridges 10.

LIQUID LEVEL SENSING AND LIQUID DISPENSING

As has been discussed above, the reaction wells 16 of the cartridge 10 contain micro-volumes of the antisera covered by a small micro-volume (approximately 2-3 $\mu l$) of oil. It is thus imperative that the liquid dispensing and liquid level sensing system used to dispense the samples to the reaction wells 16 be capable of detecting when the dispensing probe is inserted below the top surface of the oil (See FIG. 2).

In order to assure that a droplet of the sample (or other fluid being dispensed) has in fact been deposited into each reaction well 16, the apparatus preferably has the ability to detect when a droplet has been formed on the dispensing probe, when the formed droplet has separated from the dispensing probe, and when the dispensing probe has been inserted into either the oil or the serum. In the presently preferred mode of operation, the droplet is formed after the dispensing probe has been inserted into the oil or serum such that as the probe is pulled out of the liquid, the droplet of the sample will be "wiped off" of the dispensing probe. This technique combined with a closed loop system which uses the information regarding droplet formations and separations assures that a sample has in fact been deposited in each reaction well.

It will be, however, recognized by those skilled in this art that other modes of droplet formation and dispensing are possible. For example, the droplet may be formed on the dispensing probe in air before the dispensing probe is inserted into the liquid reagents.

Figure 7:
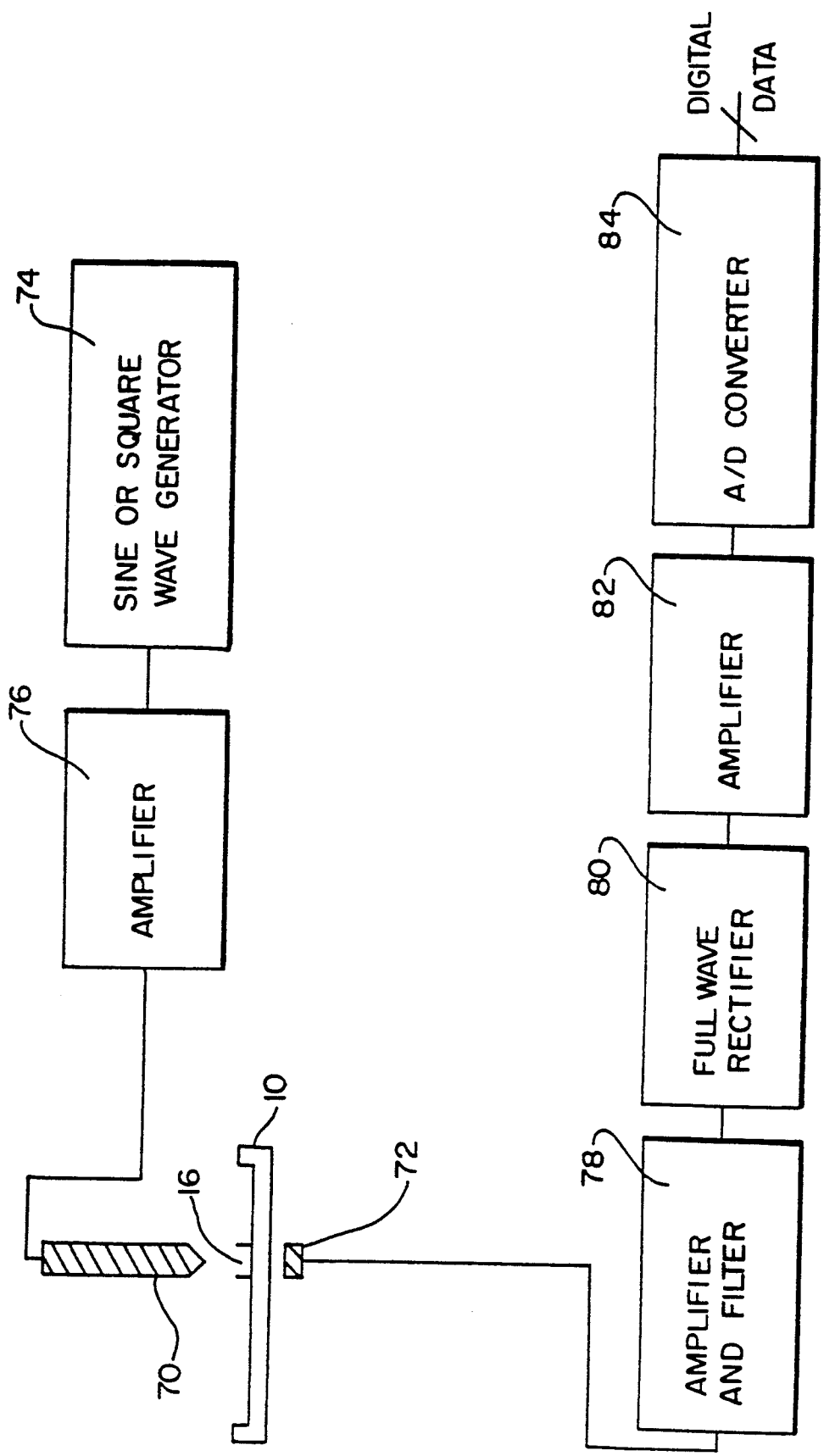
FIG. 7 is a block diagram of a preferred embodiment of the liquid level sensing and dispensing arrangement of the present invention.

A preferred embodiment of the liquid dispensing system of the present invention is illustrated schematically in FIG. 7. The liquid dispensing system includes a dispensing probe 70 for dispensing the liquid. As discussed above, the three axis robot can move the cartridge 10 in any of the X, Y, or Z directions by the use of stepper motors to position the dispensing probe 70 relative to a reaction well 16.

A sine or square wave generator (oscillator) 74 generates a radio-frequency (RF) signal which is amplified by an amplifier 76 and applied to the dispensing probe 70 which serves as a transmitting antenna. A receiving antenna in the form of a conductive element 72 is provided to receive the RF signals from the dispensing probe 70. The conductive element 72 is electrically connected to an amplifier 78. The amplifier 78 amplifies the signal received from the conductive element 72 for further processing as more fully described below. Advantageously in one embodiment, the conductive element 72 may be the magnet used in the particle separation process and working procedure described below.

The cartridge 10 is positioned such that a reaction well 16 is approximately centered below the dispensing probe 70. In a preferred embodiment, the dispensing probe 70 is about 3 mm above the bottom of the reaction well 16. In other embodiments the dispensing probe 70 may be positioned at other locations. For example, it may be disposed at the edge or rim of the reaction well such that the droplet will be dispensed on the surface of the wall of the well 16.

After the reaction well 16 is properly positioned, the monitoring of the signal from the oscillator 74 is initiated. The RF signal passes through the fluids inside the reaction well 16 and through the container and is received by the conductive element 72. The signal received by the conductive element 72 is amplified and filtered by an amplifier and filter 78. The signal is then rectified, preferably by a full wave rectifier 80, such that the output signal is a DC value corresponding to the amplitude of the received RF signal. The DC signal is then amplified by an amplifier 82 and converted to a digital signal by an analog to digital (A/D) converter 84.

Figure 8:
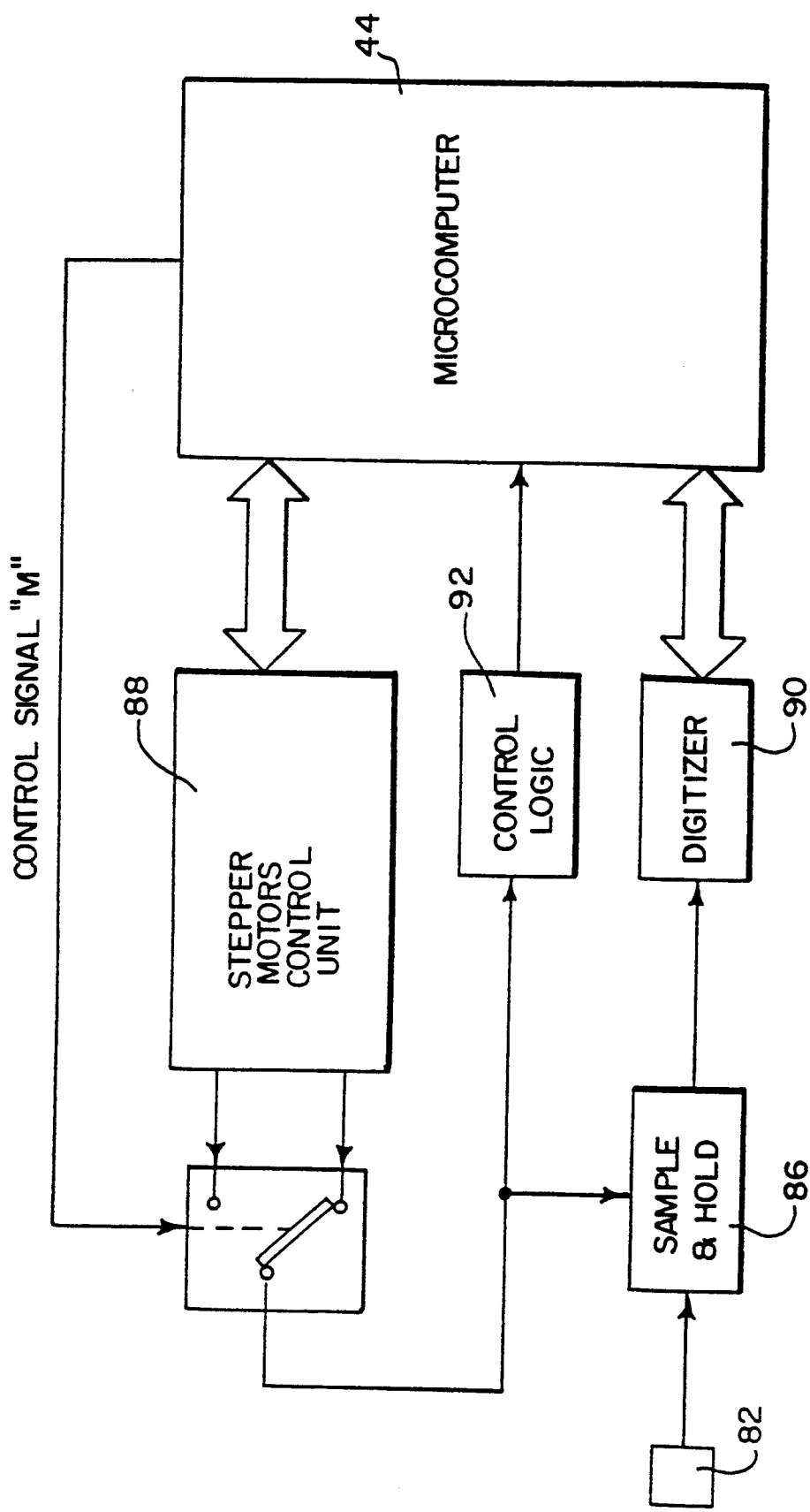
FIG. 8 is a block diagram of the control system for controlling the liquid level sensing and dispensing mechanism of the present invention.

Referring now to FIG. 8, a preferred embodiment of the control system for the liquid dispensing system is described. The DC signal which has been rectified and filtered may optionally be applied to a sample and hold circuit 86. The sample mode of the sample and hold circuit 86 occurs each time a pulse from a stepper motor control unit 88 is generated, thus providing synchronization between the DC signal value and the relative position of the sample cartridge 10. The DC signal is locked on the falling edge of the pulse from the stepper motor control unit 88 and a logical signal is sent to a digitizer 90. The digitizer 90 is preferably a twelve bit ADC. The DC signal digitized value is then stored and analyzed by the microcomputer 44 in response to a signal generated by control logic 92.

Alternatively, the system may be implemented without the sample and hold circuit 86 and the synchronization signal provided directly from the microcomputer 44.

The procedure described above of locking (from either stepper motor control or a microprocessor signal), digitizing and analyzing the DC signal with each pulse coming from the stepper motor control unit 88 continues until a sufficient difference between two consecutive stepper motor steps occurs. At this moment, the upward movement of the cartridge 10 may be stopped by a command sent to the stepper motor control unit 88. The relative position of the cartridge 10 is retrieved from the stepper motor control unit 88 by the microcomputer 44. If the relative position of the cartridge 10 is within a predetermined range (which has been stored in the memory of the microcomputer 44), then the process continues, otherwise an error condition will be reported.

After the liquid level has been identified as being within a predetermined range, the process continues with an additional movement of the cartridge 10 in the same upward direction for about 0.5 mm. During this movement, the DC signal is continuously sampled, digitized and analyzed to check for any unexpected conditions. At the end of this movement, the end of the dispensing probe 70 is reasonably assured to be inside of the oil 24 in the reaction well 16.

Next, a signal "M" from the microcomputer 44 is sent to disable the flow of pulses synchronizing with the vertical motion. The same signal "M" enables flow of the pulses synchronizing the DC signal values with a stepper motor driving and dispensing pump. A program command to run the stepper motor which drives the dispensing pump for a predetermined number of steps is issued and the DC signal value is again sampled, digitized and analyzed by the microcomputer 44. The process of dispensing a droplet continues until an adequate increase in the DC signal is encountered, or the process is terminated if there is no increase or an unacceptable increase of the DC signal value.

After the droplet has been successfully produced or dispensed, a program command is sent to the stepper motor control unit 88 to move the cartridge 10 downward. During this movement, the DC signal value is sampled, digitized and analyzed by the microcomputer 44. When the tip of the dispensing probe 70 approaches the surface of the top liquid layer, such as the oil, the process of "wiping-off" of the droplet takes place and a rapid decrease in the DC signal value is observed to confirm that the droplet has actually been separated from the probe and dispensed into the reaction well 16.

Figure 10:
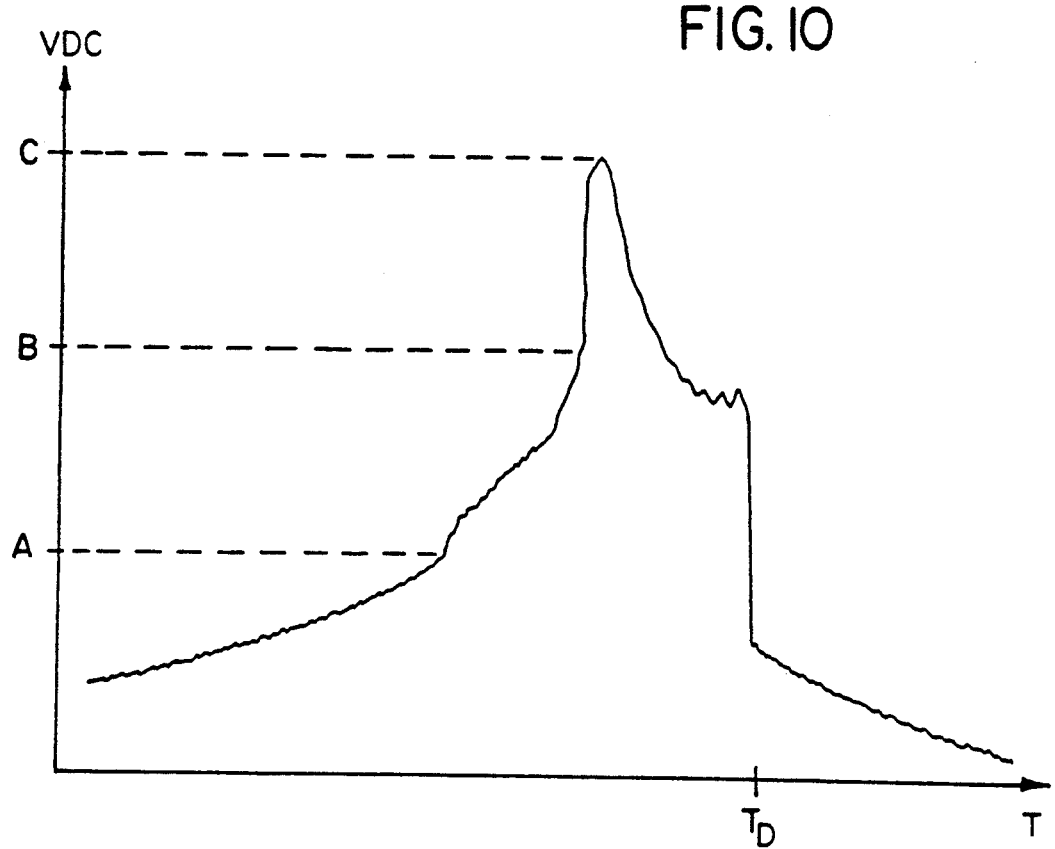
FIG. 10 is an illustration of the output signal from the liquid level detection system of the present invention for a first dispensing procedure.

The output signal $V_{DC}$ from the liquid level detecting circuit of the present invention is illustrated in FIG. 10. In the example, the probe 70 was inserted into a reaction well with reagent covered by a layer of oil and the droplet was formed in the liquid. The section of the curve from the origin to the voltage labeled "A" corresponds to the signal generated as the probe 70 approaches the upper surface of the oil. The section of the curve between the voltages labeled "A" and "B" corresponds to the signal generated as the probe 70 is advanced through the layer of oil towards the reagent. The section of the curve between the voltages labeled "B" and "C" corresponds to the formation of the droplet in the liquids. The section of the curve which decreases in slope after the voltage labeled "C" corresponds to the signal generated as the probe 70 is being withdrawn. The slope of the curve continues to decrease steadily until a time $T_D$ when the droplet is released from the probe 70 and thus the slope of the curve decreases sharply.

Figure 14:
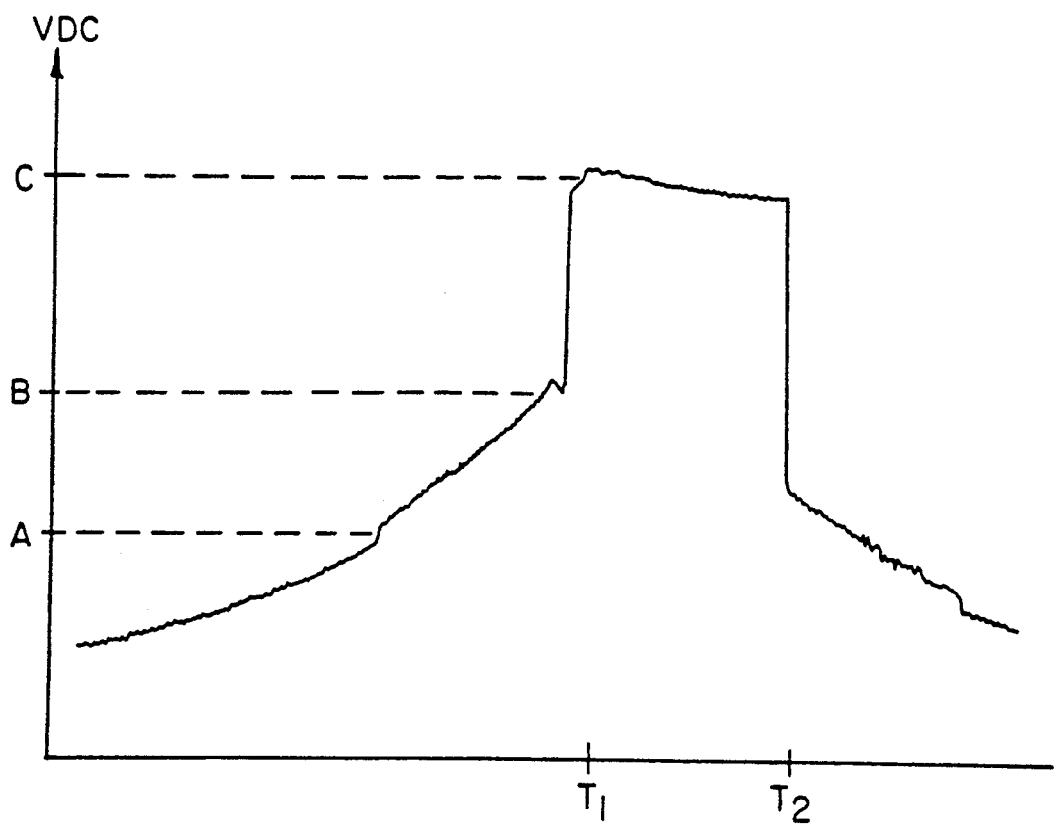
FIG. 14 is an illustration of the output signal from the liquid level detection system of the present invention for a second dispensing procedure.

It will be recognized that the signal illustrated in FIG. 14 may optionally be differentiated such that peaks may be generated and detected when there is a sharp change in slope. The differentiation may be performed by a suitable differentiating circuit or by the microcomputer 44.

Figure 9:
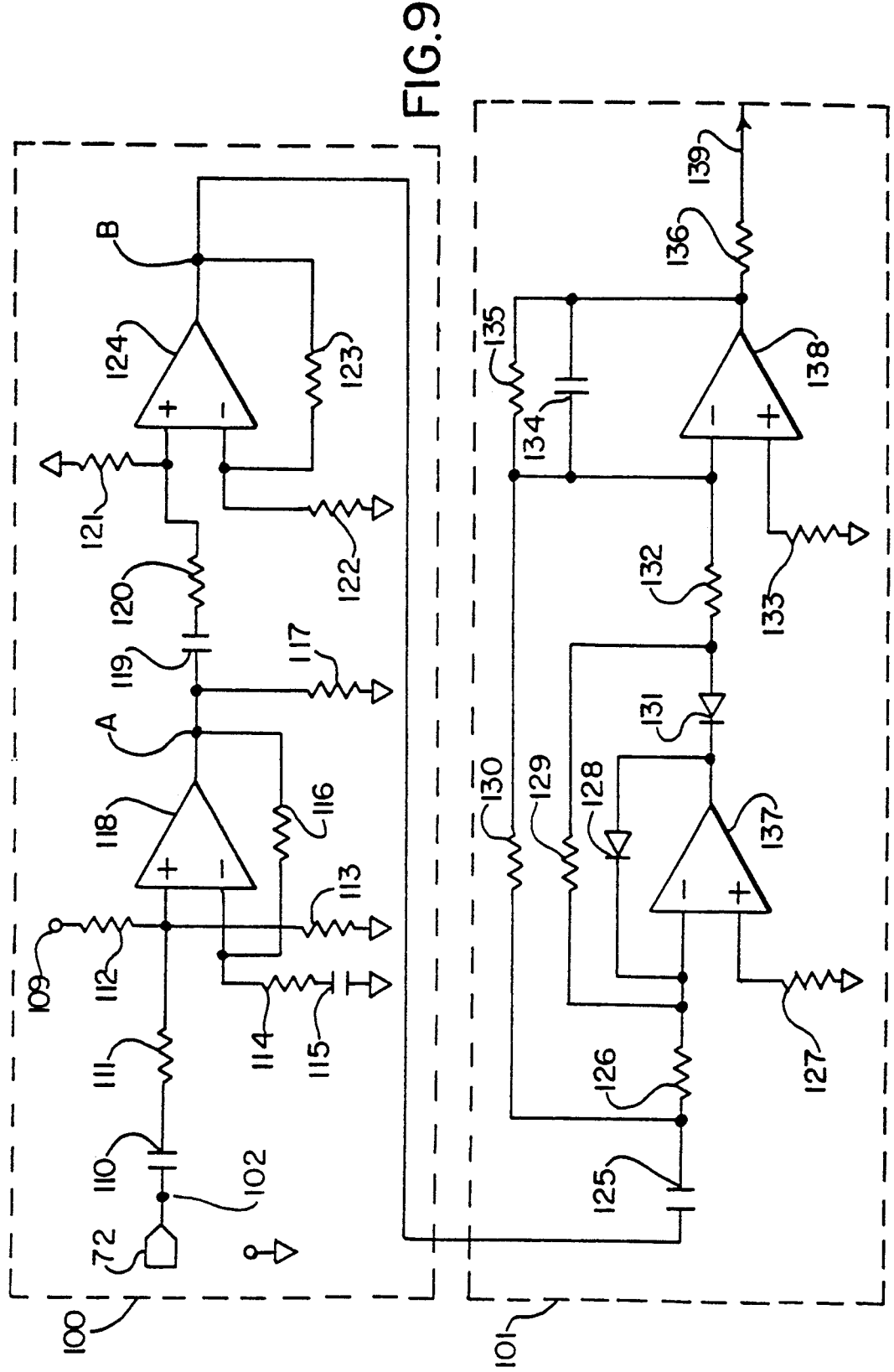
FIG. 9 is a preferred embodiment of the amplifying circuits used for the liquid level sensing and dispensing mechanism illustrated in FIGS. 7 and 8.

Next, the RF amplifying circuit will be described. As shown in FIG. 9, the amplifying circuit 100 is made up of two cascaded operational amplifiers 118 and 124. The positive input terminal of the operational amplifier 118 is connected to the conductive element 72 through resistor 111, capacitor 110 and connection 102. The positive input terminal of the operational amplifier 118 is connected to a voltage dividing circuit formed of the resistors 112, 113 keeping the output working point A at ½ of the supply voltage 109. The resistors 112, 113 and capacitor 110 act as a high pass filter to reduce circuit sensitivity to low frequency signals. The negative input terminal of the operational amplifier 118 is connected to ground through the resistor 114 and capacitor 115 and is also connected to the output terminal through the resistor 116.

A decoupling capacitor 115 allows a high AC gain of the operational amplifier 118 with unity DC gain. The AC gain of the operational amplifier 118 is defined by resistors 116 and 114.

The output terminal of the operational amplifier 118 is connected to ground through resistor 117 and is connected to the input of the operational amplifier 124 through the capacitor 119 and resistor 120. The positive input terminal of the operational amplifier 124 is also connected to ground through resistor 121. The negative terminal of the operational amplifier 124 is connected to the ground through resistor 122 and is connected to the output terminal through the resistor 123. The gain of the operational amplifier 24 is defined by resistors 123 and 122.

Next, the full-wave rectifying and filtering circuit is explained. The rectifying circuit is connected to the output terminal B of the operational amplifier 124 through capacitor 125. In the illustrated embodiment of the rectifying and filtering circuit 104 (FIG. 9), two operational amplifiers 137 and 138 have positive input terminals connected to ground through resistors 127 and 133, respectively, and the amplifiers are connected in a generally known configuration to various resistors, diodes and capacitor to produce a DC signal or lead 139.

For negative signals from the amplifying circuit 100, the output of operational amplifier 137 is clamped to 0.7 V by a diode 128 and disconnected from the negative terminal of the operational amplifier 138 by a diode 131. The operational amplifier 138 functions then as an inverter with input resistor 130 and feedback resistor 135 giving a positive signal at the output terminal of operational amplifier 138.

For positive signals from the amplifying circuit 100, operational amplifier 137 acts as an inverter with input resistor 126 and feedback resistor 132 and operational amplifier 138 operates as a summing inverter, again giving a positive output 139. When resistors 126, 129, 130 and 135 have the same value and resistor 132 is one-half the value of resistor 130, circuit 101 acts as a precision full-wave rectifier. The circuit 101 becomes an averaging filter when the time constant formed by resistor 135 and capacitor 134 is much longer than the maximum period of the input voltage which is to be averaged.

Figure 11:
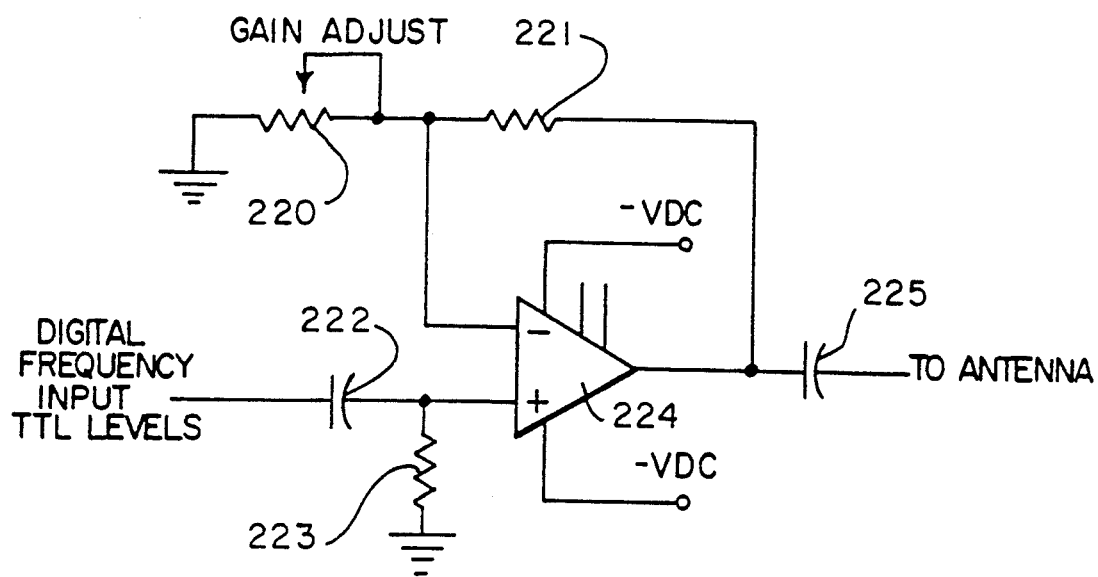
FIG. 11 is a preferred embodiment of an amplifier for amplifying the output of a square wave oscillator.

Referring now to FIG. 11, a preferred embodiment of an amplifier circuit for amplifying the output of a square wave oscillator circuit is illustrated. The amplifier circuit comprises resistors 220, 221 and 223, capacitors 222 and 225 and an operational amplifier 224. The oscillator which preferably operates at a 50 percent duty cycle, TTL levels is connected to the capacitor 222. The amplifier 224 is referenced to ground through resistor 220. A suitable oscillator is the function generator available from Wavetek as Model No. 145. The operational amplifier 224 amplifies the signal with a gain which is determined by the values of resistors 220 and 221. The output of amplifier 224 is AC coupled to the transmitting antenna through the capacitor 225.

Next, a description is given of another embodiment of apparatus and method according to the present invention. This embodiment is different from the other embodiments described above in that fluid dispensing takes place only when another fluid with a high dielectric constant has been detected. In the process described below, the two fluids have similar viscosities and thus the process will cause the two fluids to meld.

Again, the process starts with an upward movement of the cartridge 10 after a program command to move for a predetermined number of steps is issued. The upward movement continues until the oil surface is detected or end of the upward movement is detected. Once the dispensing probe 70 contacts the oil, the oil surface is detected and the program may issue a command to stop upward motion. At this time the relative position of the cartridge 10 is checked. If the relative position in the Z direction of the cartridge 10 is within a predetermined range (stored in a microcomputer memory) another program command to move cartridge 10 upward is issued. The number of steps to move upward is now equal to the predetermined value and upward movement continues until sufficient increase in the DC signal value between two consecutive stepper motor steps exists or when the end of the upward movement is detected. A rapid increase in the DC signal value manifests presence of a fluid with a dielectric constant greater than oil. The upward motion is then stopped. The dispensing process described above occurs.

FIG. 14 illustrates the signal from the detecting circuit for this embodiment. The signal at voltage level "A" represents the point where the oil surface is detected. The signal between voltages "B" and "C" at time $T_1$ represents the dispensing process when the probe touches the fluid on the bottom of the well. The signal between Times $T_1$ and $T_2$ represents a change in direction of the probe. The signal does not decrease rapidly until the oil surface is encountered. At time $T_2$ the droplet is "wipe-off" when the lower surface of the oil is reached.

OPTICS

Figure 12:
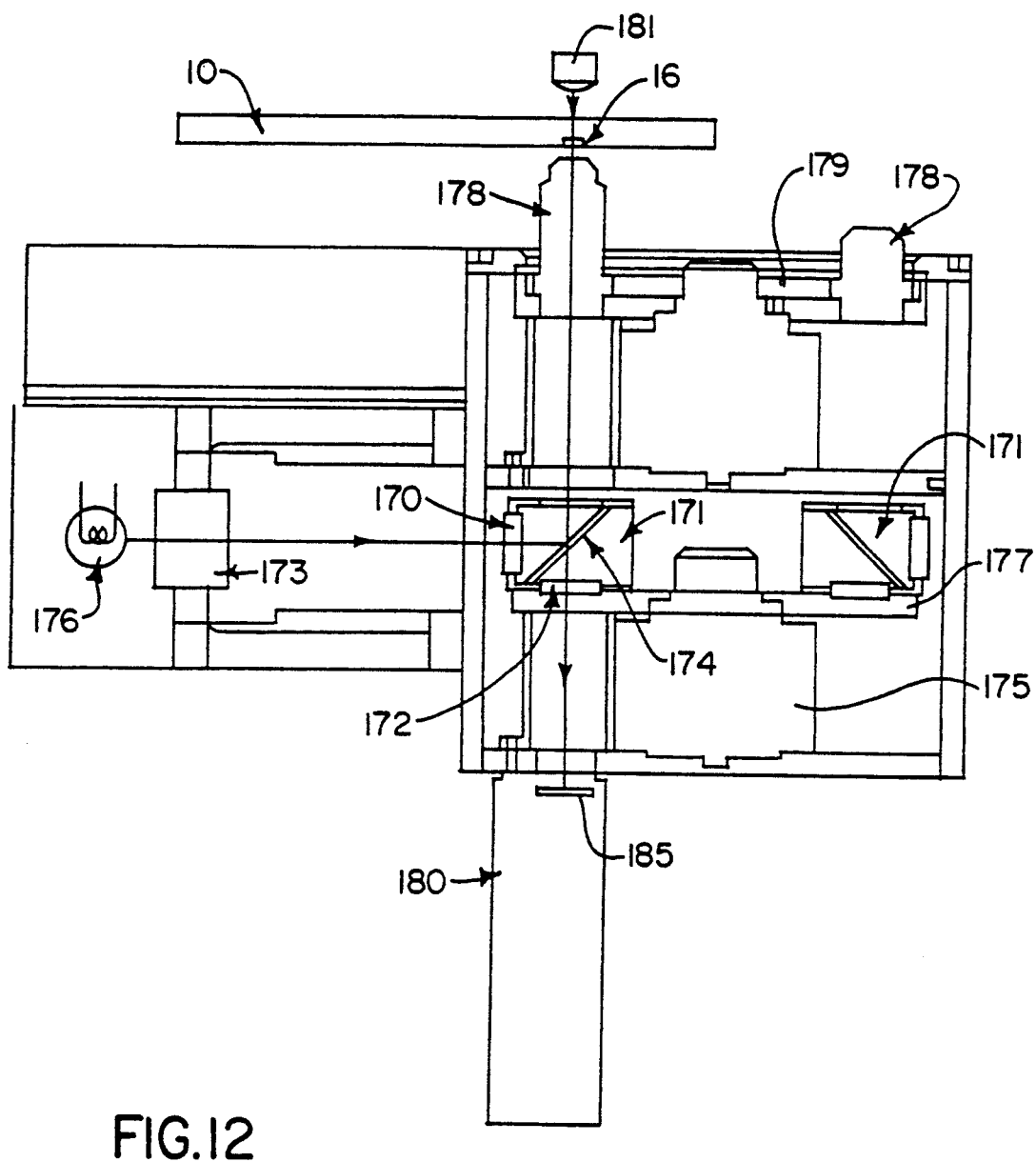
FIG. 12 is schematic of a preferred embodiment of the optical unit of the present invention.

Referring now to FIG. 12 a preferred embodiment of the optical unit for the analyzing apparatus of the present invention is illustrated. The optical unit preferably includes a turret 177 containing at least two filter blocks 171. The turret 177 is rotated by a motor 175. Each of the filter blocks 171 has an excitation filter 170, emission filter 172 and a dichroic mirror 174. A light lamp 176 which is preferably a tungsten halogen lamp provides white light. The light is passed through a condenser 173 to condense the light before it passes through excitation filter 170 and is then reflected by a dichroic mirror 174 toward the cartridge 10. The light is then provided to the reaction wells 16 through a magnifying lens or objective 178. Preferably the magnifying objective is a 10× magnifying objective. The light is then reflected by the objects reaction well 16. The light reflected from the sample well 16 passes through the objective and through the dichroic mirror 174 and then through the emission filter 172. The light transmitted through the emission filter 172 is then passed to a CCD element 185 of optical detector 180 where the light is processed as discussed in more detail below. As illustrated in FIG. 12, the arrangement is similar to an inverted microscope reading through the bottom of each reaction well 16. As illustrated, the optical system also preferably includes an objective lens turret 179 adapted to hold at least two objectives 178. The optical system may also optically include a back light source 181 (discussed in more detail below).

The filter block turret 177 preferably has a range of rotation of a full 360°, with a radius allowing up to at least 6 filter packs, such as filter packs available from Nikon (Japan), to be rotated into the imaging position. The lens block turret 179 preferably also has a 360° range of rotation with a radius allowing up to at least four standard microscope objectives, to be rotated into the imaging position. Each turret must be capable of positioning with a minimum of accuracy of +/− 0.001 inches over the entire range of rotation. Each assembled optical module must also be capable of positioning with a minimum accuracy of +/− 0.002 inches over the entire range of rotation of each turret.

As illustrated, the optical module preferably includes two direct/drive stepper motorized rotating platforms.

Preferably each axis is driven by a 400 step/rev., four phase, eight-wire stepper motor, such as one available as Model No. PX24402DA, available from VEXTA (Tokyo, Japan).

Each of the filter block and lens turret sub-assemblies preferably has a position sensor at a "home" rotational location such that the filter pack and lenses are within + or − one step of the optimum optical path as measured by the peak intensity of light into the camera with a fluorescing test image. The sensors are preferably of the non-mechanical type such as a slotted optical switch available as Model No. OPB990P51 from OPTEK (Carlson, Tex.).

For blue excitation/green emission, suitable filter packs are commercially available. A suitable filter pack, for example, is a B-2E Epi-fluorescence filter system available from Nikon (Japan). The dichroic mirror 174 preferably is positioned at 45° to the illuminator 176 and has a characteristic wavelength equal to about 510 nm. The excitation filter main wavelength preferably is 470 nm and the FWHM is about 40 nm. The emission filter 172 has a spectro-transmission range from to 520 to 560 nm.

For the green excitation/red emission, the filter pack is also commercially available such as a G-2A Epi-fluorescence filter system available from Nikon (Japan). The dichroic mirror 174 is also positioned at 45° with respect to the lamp 176 and has a characteristic wavelength equal to about 480 nm. The excitation filter 170 has a main wavelength of about 535 nm and the FWHM is about 50 nm. The emission filter 172 spectro-transmission range is from 590 nm and up.

The magnifying objective 178 is also commercially available and may be, for example, a Nikon Plan 10 DL with a numerical aperture equal to 0.25 and a working distance of 5.2 nm. This objective lens with a large numerical aperture is desirable to enhance the brightness of fluorescence images.

Preferably, the lamp color temperature for the lamp 176 is at least 3000K for the blue excitation. The lamp light output is preferably greater than 400 lumens.

It may also be advantageous to provide a neutral density filter (not shown) when using a combination of microscope objectives and relay lenses. In this embodiment, a 4.0 X perafocal magnifying objective may also be used in conjunction with the relay lenses and neutral density filter pack. A transmitting light source 181, such as an LED, may also be provided for use in reading agglutination assays.

The optical system will preferably include autofocusing means for focusing the imaging. In one embodiment which is presently contemplated, an LED 181 is used to focus on the rim of the wells. Several autofocusing algorithms for focusing with this technique are available in the art. For example one suitable algorithm is based on the "Threshold Gradient Magnitude Scheme". This algorithm is described in a paper entitled "Implementation of Automatic Focusing Algorithms for a Computer Vision System With Camera Control", Schlag et al., Carnegie-Mellon University, Aug. 15, 1983 (CMU-RI-TR-83-14), which is incorporated herein by reference.

Listed below in Table 1 are fluorophore excitation and emission wavelengths for suitable fluorophore which may be used in conjunction with the apparatus and methods of the present invention.

TABLE 1

| Fluorophore Description | Wavelengths | |
|---|---|---|
| | Excite | Emit |
| 5(6) Carboxyfluorescein Diacetate-(Mixed isomers approx. 95% by HPLC) $C_{25}H_{16}O_9$ FW 460.4 | 490 nm | 520 nm |
| Propidium Iodide- (approx. 95-98% by TLC) $C_{27}H_{34}N_4I_2$ FW 688.4 | 230 nm* 535 nm (bound)* | 602 nm |

*-exciting at bound emission frequency

IMAGE PROCESSING

As described above, the image processing unit used in the apparatus and method present invention determines the ratio of live to dead cells to which have been stained with green and red stain in each reaction well 16. The score of the reaction in each well is based on the percentage of dead cells to the total number of cells. As currently practice in the art with manual scoring, the scoring is performed using a range of 1 to 8. A score of 1 indicates that mostly live green cells which did not react with the antisera are present. Conversely, a score of 8 indicates that mostly dead cells which did not react and fluoresce red are present.

The size range of these cells of interest for HLA typing are from 6 to 12 microns in diameter, preferably with 100 to 300 cells per image. This translates into a minimum of 9 pixel areas per cell using a 512×484 resolution at 10× magnification and with bright fluorescence of some cells, a maximum of 81 pixel area for a single cell. The ratio of the average fluorescing cell image to the background mean is preferably at least 3 to 1.

Figure 13:
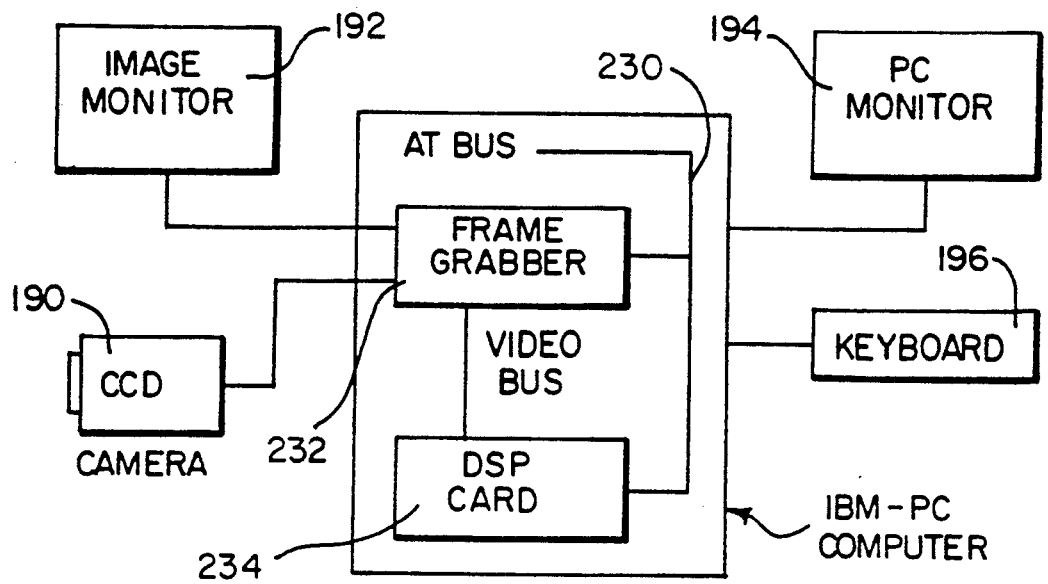
FIG. 13 is a schematic, in block diagram form, of a preferred embodiment of the image processing arrangement of the present invention.

As illustrated in FIG. 13, in the preferred embodiment, the image processing system includes a solid state charge coupled device (CCD) camera 190. The CCD camera 190 is coupled to a frame grabber 232. The frame grabber 232 preferably includes an onboard arithmetic and logic processing unit. A suitable frame grabber 232 is available from Coreco, (Montreal, Canada) as Model No. OC-300. Suitable software is also available from Coreco as a FG3 software package. The image procuring system is run by a PC computer with a display monitor 194. A suitable PC computer is an IBM AT Compatible 25 MHz 386 available from several commercial sources, such as Compaq. The system includes a monitor 192 for viewing the resulting images, such as a standard RS170 image monitor. A suitable monitor is available as Model No. VM-12016 from Hatachi Denshi, Ltd. (Woodberry, N.Y.). Advantageously, a digital signal processing (DSP) card 234 is expected to significantly increase the system performance (discussed in more detail below). The DSP card 234 is expected to increase the throughput of the frame grabber 232 alone by a factor of 6. That is, using the frame grabber 232 alone, processing would take at least 4 seconds per image. With the DSP card 234 processing is expected to take less than ½ second.

Although data from the frame grabber 232 may be transferred to the DSP card 234 via the standard AT bus, this places a heavy load on the main microcomputer. Therefore the DSP card 234 is preferably connected to the frame grabber 232 via a video bus (illustrated in the dotted line). This frees the main processor for other tasks.

A CCD camera which has proved suitable for use in the present invention is Model No. KP110 available from Hatachi Denshi, Ltd. (Woodberry, N.Y.).

The following describes several algorithms which may be used in the image processing stage of the present invention. In one embodiment, the FG3 software may be used to control both the range/offset and live/capture operations of the frame grabber. The range and offset may be, for example, typically set 16 and 32 respectively, shifting the value of zero 32/256 of full scale, and expanding 16/256 of the range to maximum intensity. It has been found that these values yield the highest contrast images with the least amount of noise. Once the image is focused as described above, the image is grabbed, then saved. From this point on, all processing may be done completely in computer RAM, with the results displayed on either an EGA or VGA screen.

A row normalization technique may be used to compensate for background light gradients. Each row of data (512 points) is summed, then divided by 512 and stored as the baseline for that row during thresholding. The total image normalization (row and column) at any point is the average of the row mean and the column mean at that point subtracted from the raw value at that point. To prevent any negative values, this may be implemented here by adding the (row) mean to a manually entered threshold.

A nearest neighbor filter convolution technique may be used to eliminate small "salt and pepper" noise from the image. For cells which are essentially round and at least 9 pixels in area, based on the 10× magnification, ⅓" size of the CCD element and a 6–12M cell size, there is no interest in pixels that do not have neighboring pixels of greater intensity than a given threshold.

As will be recognized by those skilled in the art, there are many different kernels, or weighings, for this type of filtering. One approach which may be used will require any pixel to have at least one other pixel either above or below its position (either directly or diagonally) above the selected threshold, or the pixel value became zero. This eliminates all single pixel noise elements, and requires all "surviving" elements to be two dimensional.

A more general approach is typically a 3×3 kernel "K" mapped over a 3×3 area of the image "I", where each pixel is multiplied by the weighing in the corresponding value in the kernel. The results are summed, then divided by the total weighing.

Once the image has been normalized and filtered using the normalized value as the threshold, the algorithm preferably prompts for a manually selected threshold. This is determined by looking at the color of the background and comparing the brightest background color with the colorbar. Each color of the color bar has a value of 16 gray scale intensities in the original image. This value generally assures that all background is eliminated, at the possible expense of shrinking some weaker cells, depending on contrast and focus. Some experimentation may be needed to yield the best selection with minimum data loss. For example, the value 48 has been shown to work well with this approach.

Once all parameters have been selected, a "reverse fill" algorithm may be used to scan the image. This reverse fill algorithm scans from top left to right, and stop when the first non-zero pixel is detected. A counter is then preferably initialized and incremented as the search continues on that line until a (zero) background pixel is detected. The search then moves back to the first pixel, down one row, and searches to the left for the first background pixel. Since prior filtering has guaranteed that all elements are two-dimensional, this method is acceptable. When the left-most non-zero pixel has been detected, the counter again is incremented until the right-most pixel has been reached. This process continues for each succeeding row until there are no further pixels below the last row checked.

This approach works well as long as the elements are more or less round, as are cells in the HLA assay. However, if cell clusters or other nonround elements are in the image, this version of the algorithm may have some shortcomings, especially in a horizontal large and small "dumbbell" type of element, where the large element on the left is properly sized except for a center row, but the right element will be split in half. Although these and other similar errors are possible, cell sizing and subsequent counting has been found to yield scoring comparable to human readings.

As each pixel is counted, its color is changed to the bright value by adding 8 to the selected binary color. Once the processing of the element is completed, its size is compared to the selected range. If the cell falls within that range, the process is repeated, changing the color to bright white (color-15). Raster scanning then continues looking for the start of the next element until the entire image has been searched.

Although this technique is suitable, it is very time consuming, and filling time is added to border detection time, causing even more overhead.

The above-described algorithms may be used on a system with either a VGA or EGA display card. If an EGA display card is used some modifications may be necessary since an EGA display card has 640×350 pixel by 16 color resolution and the images grabbed are 512×484 pixels by 256 gray scale. The wide variation between the aspect ratios will distort the cells to appear vertically elongated rather than round. This may be solved by duplicating each pixel twice in the x-axis, giving a viewing window of 320×350, or nearly a one to one aspect ratio. The gray scale intensities may shifted to the right 4 bits, or divided by 16, and then mapped onto the 16 available colors. If desired, this pseudo-color mapping may also be used in the Video Graphics Adaptor (VGA) where the available 640×480 resolution no longer presents an aspect ratio problem, and the full raw image may be displayed.

In another embodiment, a "contour feature extraction" algorithm is used. There are two primary differences between the "reverse-fill" algorithm and the "contour feature extraction" approach. Both scan the image from top left to right for the first non-zero element. The contour algorithm then creates a vector map of the perimeter of the element by searching counter-clockwise for adjacent, unhighlighted pixels until the contouring is completed. The size of the element is then calculated from the vector map.

This technique, however, also highlights only the perimeter of each element, rather than every pixel in each element. This, combined with processing in the frame grabber 232 rather than disk swapping of raw image data, and the ability to perform a full-frame manually selected threshold binarization while executing the contour sizing/counting algorithm greatly improve throughput and eliminate errors due to element shape. The contour feature extraction algorithm works well with a even background, high contrast image. The algorithm, however, requires manual selection of threshold, and does not take into account any background light gradient or other filtering, all of which are desirable for automated scoring.

In another embodiment, the frame grabber 202 is used for real time image averaging. This technique sums a selected number of frames of image data on the fly, keeping the intermediate results in the second frame buffer. It has been found that, for images of interest in assay procedures, averaging two to four frames yields a substantial improvement in signal to noise (cells to background) allowing these images to be used without further filtering. This dramatically increases throughput without adding processing overhead to the main computer.

It is also desirable in automated scoring to have the ability to perform localized auto-thresholding and binarization within windows of the image. This may be performed using software available from Coreco by performing statistical analysis on a window of user-specified size, for example 32×32 pixels, and deciding whether any cells exist in the window by looking at the peaks of the histogram of the window. If only one peak exists, than this is assumed to be the background peak, and no cells are in that region. If two peaks are detected, than a threshold is selected by a user-selectable percent distance between the background and foreground peaks, and this value is used to binarize the window. From here, the contour sizing/counting algorithm described above may be used to complete the autoscoring of the reaction wells 16.

In the most preferred embodiment, the DSP card 234 is used to perform high speed auto-thresholding and binarization. The DSP card 234 preferably includes a processor with a parallel high speed multiplier and adder and separate instruction and data busses.

As discussed briefly above, in one embodiment the frame grabber 232 captures the images and transfers them across the AT main computer bus in small blocks to a DSP input buffer. As the DSP receives the data, it performs all operations for determining the threshold automatically, binarizes the image, and compresses the elements to be sized and counted. As processing of each element is completed, the results are placed in the DSP output buffer. From there, the final sizing and counting are performed by the main computer.

More preferably, the data is transferred directly from the frame grabber 232 via a video bus. This frees the main computer for other tasks and takes full advantage of the multi-processor configuration.

OPERATION OF THE APPARATUS

Operation of the apparatus of the present invention is now described for HLA typing. The operator first isolates the cells of interests by known techniques (such as by the Ficoll Hypaque method). Since the reaction cartridges 10 will typically be provided with the reagents in a frozen state, the operator thaws the cartridge 10. The cartridge 10 preferably has a preprinted barcode containing assay type and other information. The operator then logs in the patient data by typing in the patient information using the microcomputer keyboard.

The operator places paramagnetic beads and a fluorophore into well 12 of cartridge 10 for dispensing by a pipette. 50 microliters of the sample cells are then pipetted manually by the operator into the sample well 11a, 11b or both. The operator then loads the cartridge 10 into the automated instrument in the load area 30. One of the pipette robot 34 and image robot 40 then moves the cartridge 10 to a barcode reader to read the information on the preprinted cartridge barcode.

The pipette robot 34 then retrieves the cartridge 10 and moves it under a pipette. The pipette then adds 50 $\mu$l of paramagnetic beads and green fluorophore to the sample cells from the well 12. A suitable green fluorophore is the 5(6) Carboxyfluorescein disclosed in Table 1. The mixture is then incubated in the incubation area 38 for 10 minutes at ambient temperature. The pipette robot 34 then retrieves the cartridge 10 and moves it to a pipette.

A magnet, such as a rare earth magnet (Permag, Ill.), is then placed under the sample well to hold the cells which have not attached to the paramagnetic beads and to act as the conductive element 72. The sample wells 11a, 11b are then washed to wash off uncaptured cells. 70 $\mu$l are aspirated from each of the sample wells 11a, 11b into the waste blotter and an equal volume of buffer is added to sample well 16. This washing step is repeated 3 to 4 times, leaving a final volume of 100 $\mu$l.

The magnet is then removed and the cells are mixed in the sample well 11a, 11b. 0.5 $\mu$l of cells are then pipetted into one of the reaction wells 16 on the cartridge 10. The cells are counted in this reaction well using a CCD and read at 490 nm. If the cell number is inadequate a signal is given to the operator and the cartridge is rejected. If the cell number is too high, the number of cell is estimated and must be diluted.

If the cell number was adequate or the cell number has been diluted, 0.5 $\mu$l of the cells are dispensed into each reaction well 16. The cartridge 10 is then moved to the incubator area 38, which is at ambient temperature, for approximately 30 minutes. A rehydrated complement/red fluorophore mixture with 480 $\mu$l of buffer are provided to the pipette. A suitable red fluorophore is the propidium iodide disclosed in Table 1. The cartridge 10 is moved to the pipette which then dispenses 3 $\mu$l of the complement per reaction well 16. After all of the reaction wells 16 have been completed, the cartridge 10 is moved to the incubator area 38 and incubated at ambient temperature for 30 to 45 minutes, depending on the samples being analyzed. Optionally, the pipette may dispense 50 $\mu$l of buffer per reaction well 16. The cartridge 10 is then retrieved by the image robot 40 and each well is image processed at 490 nm/540 nm and the results and/or image is then stored. After the samples have been image processed (the cells have been counted and scored), the cartridge 10 is then moved to an unload area 46 where it is unloaded manually by an operator.

EXAMPLES

The following examples are given to illustrate more specifically use of the apparatus and methods of the present invention.

EXAMPLE 1

HLA Typing by Two Color Fluorescence Using Complement Dependent Microlymphocytotoxocity For Image Analysis Referring to FIG. 1, wells 11a and 11b designate reservoirs for holding leukocyte suspension for which a HLA determination was to be carried out. Lymphocyte purification was carried out using paramagnetic particles purchased from Advanced Magnetics Inc. (Cambridge, Mass.) (under the BIOMEG tradename) conjugated with CD2, or CD8 monoclonal antibodies according to the published procedures (Vartdal F. et al., Tissue Antigen 1986; 28: 30–1312). For Class II typing, monoclonal antibody such as L243 could be conjugated to similar paramagnetic particles purchased from Advanced Magnetics Inc. (Cambridge, Mass.). After the initial manual loading of purified lymphocyte suspension into one of the two sample wells 11a or 11b, all subsequent steps were handled by the apparatus of this invention. Reagents including typing sera, paramagnetic particles and 5,6 carboxyfluorescein diacetate (Sigma, Mo.) mixture, lyophiled complement (Pel Freeze, Milwaukee, Wis.) and propidium iodide (Sigma, Mo.) mixture that were necessary to complete a Class I or II HLA Typing were included on the cartridge 10. A volume of 100 μl of the paramagnetic particles and 5,6 carboxyfluorescein diacetate mixture was pipetted into 100 μl of lymphocyte sample. After 10 minutes incubation at room temperature, the stained and rosetted cells were then separated from the uncaptured leukocytes by placing the underside of the well against a rare earth (Permag, Ill.) magnet for 15 second. Rosetted cells were subsequently washed with three changes of 300 μl of 1 TDX ® buffer (Abbott Labs, Ill.) while keeping the rosettes in place by the above-mentioned magnetic device. A minimum of 0.5 μl of rosetted leukocytes was pipetted into reaction wells 16 containing at least 0.5 μl of HLA typing serum submerged in 2.5 μl of mineral oil. At the end of the 30 minute incubation period, a minimum of 3 μl of rabbit serum containing 2 mg/ml of Propidium iodide was added to each of the reaction well 16. The reaction was allowed to incubate for an additional 30 minutes at room temperature. Positive reactions were indicated by varying degree of lympholysis. 5,6 CDF stained cells were viewed under a set of excitation (450 to 490 nm) and emission (520 to 560 nm) filter (Nikon, Japan), while the PI stained cells could be observed using a set of excitation (510 to 560 nm) and emission filter (590 nm).

EXAMPLE 2

Immunocytochemical Staining of Labeled Cells for Biologic Markers in Biopsy Materials Or Tissue Sections In another assay, human estrogen receptor expression on normal and malignant breast tissues using immunoperoxidase cytochemical method was used. Tissues were harvested and prepared according to the Abbott-ER-ICA Monoclonal Assay (Abbott Labs, Abbott park, Ill.) using immunoperoxidase reaction. The nuclei of the cells that did not contain a significant amount of estrogen receptor would show up light blue. In contrast, tumor cells with elevated estrogen receptor expression would appear reddish brown. Applications of this technique can be extended to other cellular, or subcellular biologic markers in conjunction with insitu hybridization technique using DNA/RNA probes or other immunostaining methodologies including various isotopes, chemical stains, immunologic reagents, or enzyme/substrate combinations. Biologic markers can include protein, carbohydrate, lipid or any of these combinations. Specimen can either be a blood smear; biopsy materials or cytologic smears; or thin tissue sections prepared by chemical fixation, frozen, or paraffin section methodologies according to standard methodologies.

EXAMPLE 3

Front Surface Immunoassay For Analyte Determination

As discussed in more detail below, a significant advantage of the present invention is the ability to upgrade the device to perform different types of assays. For example, the apparatus and method of the present invention may be used to enhance the precision and sensitivity of fluorometric or coloramatric immunoassays. In one example of a different assay type, reactions are carried out in a 96 well microliter-carriage (Abbott Labs, Abbott Park, Ill.) Reagent mixing, incubation and signal development occur in the reaction wells. In the sample reaction, paramagnetic particles are coated with mouse IgG by procedures known to those skilled in the art. Goat anti-mouse labeled with B-Galactosidase is used for detecting the mouse IgG. To start a reaction, 50 μl of mouse IgG coated paramagnetic particles are mixed with equal volume of goat anti-mouse-B Galactosidase complex in the reaction wells for twenty minutes at room temperature. The unbound goat anti-mouse-B Galactosidase complexes are washed away with a total of 500 μl of TDX ® buffer (Abbott Labs, Abbott Park) while the paramagnetic particles are held in place with a magnet. A volume of 50 μl of a fluorogenic substrate such as Di-B-Galactosylfluoroscein (Sigma, Mo.) are added to the particles. Fluorescence densitometry or absorbance changes may be monitored through the image analysis arrangements described above.

FIELD UPGRADES

The apparatus and method of the present invention provide significant advantages over the prior art devices. These advantages have been described in part throughout the text of the above description. Another significant advantage, which is described in more detail here, resides in the expandability of the apparatus to perform different assays, and the minimum amount of modifications which must be made to upgrade the apparatus in order for the device to perform different assays.

As discussed above, variation in sample preparations and other anomalies limit the usefulness of most, if not all, available systems since these systems require major hardware redesign to accommodate these variations. Further, available automated assay instruments are dedicated to a single type of assay. Again, major hardware redesign is needed to upgrade the instrument to perform assays other than the one it was originally designed for.

The system of the present invention provides an arrangement which does not have these limitations. The apparatus and method of the present invention can be easily reconfigured to accommodate variations in an assay test or to perform different assays. The modification will simply require changing the optical filters and objectives and/or modifying the algorithms for the image processing and other minor modifications. The algorithm can be developed and the appropriate filters and objectives selected before the field upgrade is performed. As will be appreciated these modifications or upgrades can then be performed in the field without a significant amount of effort by the person performing the upgrade in the field.

Since the assay steps are performed automatically, a significant amount of human operator time is also eliminated. It is expected that an HLA assay performed using the instrument of the present invention will result in a saving of between 63%-80% of the operator time required to perform the steps manually.

The foregoing description of the preferred embodiments has been presented for purposes of illustration and description. They are not intended to be exhaustive or to limit the invention to the precise forms disclosed. It is intended that the scope of the invention be defined by the following claims including all equivalents.

We claim:

1. A method for sensing the level of a liquid in a container relative to a dispensing probe, said method comprising:

spacing the probe and a receiving antenna a fixed distance apart such that the container may be inserted into a space between the probe and the receiving antenna;

inserting a container with fluid therein into the space;

applying a radio frequency signal to the probe whereby it radiates a radio frequency signal that is sensed by the receiving antenna;

moving the container relative to the probe;

converting the signal sensed by the receiving antenna into a further signal representing the magnitude of the sensed signal; and, analyzing the further signal to determine changes in the magnitude of the sensed signal as an indication of the level of the liquid in the container as the container is moved relative to the probe.

2. A method as claimed in claim 1 and further comprising controlling movement of said container in accordance with changes in the magnitude of the sensed signal.

3. A method as claimed in claim 1 wherein the step of converting the signal sensed by the receiving antenna into a further signal comprises converting the sensed signal into a digital signal.

4. A method as claimed in claim 1 wherein the step of converting the signal sensed by the receiving antenna comprises rectifying the sensed signal to produce a DC signal and converting the DC signal to a digital signal.

5. A method as claimed in claim 2 and further comprising the step of:

determining the time rate of change of said further signal as the container is moved relative to the probe.

6. A liquid level sensing device for sensing the level of a liquid in a container relative to a dispensing probe, said device comprising:

a receiving antenna spaced a fixed distance from said probe such that the container may be inserted between the probe and the receiving antenna;

means for inserting the container into the space and moving it relative to the probe;

a radio frequency signal generator means connected to the probe whereby the probe radiates a radio frequency signal that is sensed by the receiving antenna;

converter means for converting the signal sensed by the receiving antenna into a further signal representing the magnitude of the sensed signal; and, analyzer means for analyzing the further signal to determine changes in the magnitude of the sensed signal as an indication of the level of the liquid in the container as the container is moved relative to the probe.

7. A liquid level sensing device as claimed in claim 6 and further comprising means responsive to said analyzer means for controlling movement of said container.

8. A liquid level sensing device as claimed in claim 6 wherein said converter means includes means for converting the sensed signal into a digital signal.

9. A liquid level sensing device as claimed in claim 6 wherein said converter means comprises a rectifier for converting the sensed signal to a DC signal and means for converting the DC signal to a digital signal.

10. A liquid level sensing device as claimed in claim 7 wherein the means for moving the container relative to the probe comprises means for moving the container toward and away from the probe.

11. A liquid level sensing device as claimed in claim 7 wherein the means for analyzing the further signal comprises means for determining the time rate of change of the further signal.

12. A liquid level sensing device as claimed in claim 6 wherein the radio frequency signal generator means comprises means for generating a sine wave.

13. A liquid level sensing device as claimed in claim 6 wherein the radio frequency signal generator means comprises means for generating square wave pulses at a radio frequency.

14. A liquid level sensing device for sensing the level of a liquid in a container relative to a dispensing probe and controlling motion of the container relative to the probe, said device comprising:

a receiving antenna spaced a fixed distance from said probe such that the container may be inserted between the probe and the receiving antenna;

a radio frequency signal generator means connected to the probe whereby the probe radiates a radio frequency signal that is sensed by the receiving antenna;

converter means for converting the signal sensed by the receiving antenna into a digital signal representing the magnitude of the sensed signal as an indication of the level of the liquid in the container; and, means responsive to the digital signal for controlling movement of the container relative to the dispensing probe along at least one axis.

15. A liquid level sensing device as claimed in claim 14 wherein the container is a multi-container or reaction well cartridge, and said means responsive to the digital signal for controlling movement of the container comprises means for moving said container along three mutually perpendicular axes.

* * * * *